(12) United States Patent
Sato et al.

(10) Patent No.: US 7,816,558 B2
(45) Date of Patent: Oct. 19, 2010

(54) TRIARYLCARBOXYLIC ACID DERIVATIVE

(75) Inventors: Junji Sato, Tokyo (JP); Kazuyuki Hattori, Tokyo (JP); Hirokazu Kubota, Tokyo (JP); Ryosuke Munakata, Tokyo (JP); Toru Asano, Tokyo (JP); Junko Maeda, Tokyo (JP); Masakatsu Kawakami, Tokyo (JP); Akio Kamikawa, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 469 days.

(21) Appl. No.: 11/910,072

(22) PCT Filed: Oct. 6, 2006

(86) PCT No.: PCT/JP2006/320061

§ 371 (c)(1),
(2), (4) Date: Sep. 28, 2007

(87) PCT Pub. No.: WO2007/043457

PCT Pub. Date: Apr. 19, 2007

(65) Prior Publication Data

US 2009/0018104 A1    Jan. 15, 2009

(30) Foreign Application Priority Data

Oct. 7, 2005    (JP)    ............... 2005-295740

(51) Int. Cl.
| C07C 63/33 | (2006.01) |
| C07C 321/00 | (2006.01) |
| C07D 277/04 | (2006.01) |
| C07D 333/62 | (2006.01) |
| C07D 231/10 | (2006.01) |
| C07D 211/78 | (2006.01) |
| A01N 43/40 | (2006.01) |
| A01N 43/82 | (2006.01) |
| A01N 43/06 | (2006.01) |

(52) U.S. Cl. ................. 562/492; 548/146; 548/373.1; 549/29; 546/318; 514/277; 514/362; 514/363; 514/438

(58) Field of Classification Search ........... None
See application file for complete search history.

(56) References Cited

U.S. PATENT DOCUMENTS

| 4,539,328 | A | 9/1985 | DiMenna et al. |
| 4,891,057 | A | 1/1990 | Sohn et al. |
| 5,614,520 | A | 3/1997 | Kondo et al. |
| 2004/0214888 | A1 | 10/2004 | Matsuura et al. |

FOREIGN PATENT DOCUMENTS

| EP | 0 513 379 A1 | 11/1992 |
| JP | 57-85379 | 5/1982 |
| JP | 59-95272 | 6/1984 |
| JP | 6-65210 | 3/1994 |
| JP | 6-211815 | 8/1994 |
| JP | 10-310578 | 11/1998 |
| JP | 2000-1431 | 1/2000 |
| JP | 2002-105067 | 4/2002 |
| WO | 92/09279 | 6/1992 |
| WO | 96/31211 | 10/1996 |
| WO | 98/18765 | 5/1998 |
| WO | 2006/022374 | 3/2006 |
| WO | 2006/022375 | 3/2006 |

OTHER PUBLICATIONS

Database CAS citation 2006:196056 [retrieved Feb. 3, 2010] from STN; Columbus, OH, USA.*
Ishibuchi, Seigo et al., "Synthesis and Structure-Activity Relationships of 1-Phenylpyrazoles as Xanthine Oxidase Inhibitors", Bioorganic & Medicinal Chemistry Letters, vol. 11, pp. 879-882, 2001.
Salman, A.S.S., Synthesis and reaction of cyanopyridone derivatives and their potential biological activities, Pharmazie, vol. 54, pp. 178-183, 1999.
Finn, John et al., "Discovery of a Potent and Selective Series of Pyrazole Bacterial Methionyl-tRNA Synthetase Inhibitors", Bioorganic & Medicinal Chemistry Letters, vol. 13, pp. 2231-2234, 2003.

* cited by examiner

*Primary Examiner*—Karl J Puttlitz
(74) *Attorney, Agent, or Firm*—Oblon, Spivak, McClelland, Maier & Neustadt, L.L.P.

(57) ABSTRACT

Provided is a triarylcarboxylic acid derivative, or an isomer, a prodrug, a hydrate, a solvate, a polymorph, or a pharmaceutically acceptable salt thereof, represented by the following general formula (I):

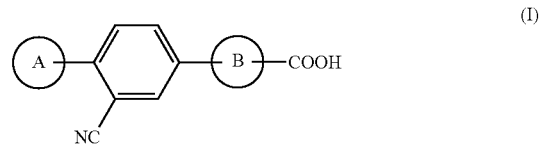

(I)

wherein A is an optionally substituted aryl or heteroaryl, and B is an optionally substituted monocyclic heteroaryl; and a pharmaceutical composition comprising the same and a pharmaceutically acceptable carrier. The triarylcarboxylic acid derivative (I) exhibits potent xanthine oxidase inhibiting action and is therefore useful as a therapeutic agent for preventing or treating hyperuricemia, gout, inflammatory bowel disease, diabetic nephropathy and diabetic retinopathy.

19 Claims, No Drawings

TRIARYLCARBOXYLIC ACID DERIVATIVE

TECHNICAL FIELD

The present invention relates to a triarylcarboxylic acid derivative useful as medicines, especially as an agent for treating or preventing xanthine oxidase-related diseases such as hyperuricemia, gout, inflammatory bowel disease, diabetic nephropathy, diabetic retinopathy, etc.

BACKGROUND ART

Abnormal increase in blood uric acid level, i.e., hyperuricemia is a disorder that has close relation to gout, renal dysfunction, urolithiasis, etc. (Diagnosis and Treatment, 2002, 90(2), 244-248; Diagnosis and Treatment, 2002, 90(2), 220-224). It is known that, in organ transplantation (Ren. Fail. 2002 May; 24(3):361-7) or chemotherapy for cancer (Am. J. Health Syst. Pharm. 2003 Nov. 1; 60(21):2213-22), serum uric acid level extremely increases, thereby causing renal dysfunction (tumor lysis syndrome). An agent for treating hyperuricemia may be roughly classified into an uricosuric agent and an uric acid synthesis inhibitor. The uricosuric agent may be ineffective for cases whose renal function has lowered, and therefore allopurinol (Nippon Rinsho, 1996 December; 54(12): 3364-8, and Nippon Rinsho, 2003; 61, Suppl. 1: 197-20), an uric acid synthesis inhibitor, is suitably used for patients having a lowered renal function (Guideline for Treatment for Hyperuricemia, Gout; Treatment Guideline by the Gout/Nucleic Acid Metabolism Society of Japan, 2002). Xanthine oxidase is an enzyme that controls the biosynthesis of uric acid, and a xanthine oxidase inhibitor to inhibit this enzyme is effective for treatment of hyperuricemia and various diseases caused thereby, as an uric acid synthesis inhibitor. Allopurinol is only one xanthine oxidase inhibitor that has been put into practical use at present for clinical treatment.

On the other hand, it is known that xanthine oxidase plays a role as an active oxygen producing enzyme (Drug Metab. Rev. 2004 May; 36(2): 363-75). Active oxygen is a precipitating factor for pathology, as damaging DNA and cells and as inducing inflammatory cytokine production (Free Radic. Biol. Med. 2001 May 15; 30(10): 1055-66). For example, it is known that active oxygen is concerned deeply with autoimmune inflammatory diseases such as ulcerative colitis and Crohn's disease (Scand. J. Gastroenterol. 2001 December; 36(12): 1289-94), and ischemic reperfusion disorder (Biochem. Biophys. Res. Commun. 2004 Mar. 5; 315(2): 455-62). Further, recently, it has been suggested that active oxygen may participate in diabetic nephropathy (Curr. Med. Res. Opin. 2004 March; 20(3): 369-79), cardiac failure (J. Physiol. 2004 Mar. 16; 555 (Pt 3): 589-606, Epub 2003 Dec. 23), cerebrovascular disorder (Stroke, 1989 April; 20(4): 488-94), etc., as one precipitating factor for them. It is known that, in diabetic retinopathy, the increase in the vascular endothelial growth factor (VEGF) level in a vitreous body is deeply concerned with pathologic deterioration, and during the disease, there occurs VEGF expression increase via oxidation stress (Curr. Drug Targets, 2005 June; 6(4): 511-24). A xanthine oxidase inhibitor inhibits the production of active oxygen, and this is therefore effective for treatment for these diseases. In fact, it is reported that allopurinol is effective for human ulcerative colitis (Aliment. Pharmacol. Ther. 2000 September; 14(9): 1159-62), diabetes-accompanied vascular disorder (Hypertension, 2000 March; 35(3): 746-51) and chronic cardiac failure (Circulation, 2002 Jul. 9; 106(2): 221-6).

Thus, the effectiveness of allopurinol, a xanthine oxidase inhibitor, for various diseases is reported, but on the other hand, its serious adverse side effects such as Stevens-Johnson syndrome, toxic epidermal necrolysis, hepatopathy and renal dysfunction are also reported (Nippon Rinsho, 2003; 61, Suppl. 1: 197-201). It is pointed that one cause of it is that allopurinol has a nucleic acid-analogous structure and inhibits a pyrimidine metabolic pathway (Life Sci. 2000 Apr. 14; 66(21): 2051-70). Accordingly, development of a non-nucleic acid structure xanthine oxidase inhibitor having higher safety and having potent medicinal efficacy is earnestly desired.

Hithertofore, compounds having a xanthine oxidase inhibitory activity are known. For example, 2-phenylthiazole derivatives of the following general formula are reported (Patent Reference 1):

[Formula 1]

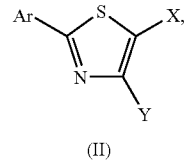

(II)

Ar represents

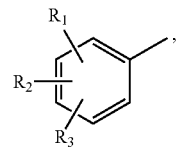

etc.

(wherein $R_1$, $R_2$ and $R_3$ each independently represent a hydrogen atom, a halogen atom, a nitro group, a cyano group, a formyl group, a $C_{1-4}$ alkyl group, a $C_{1-4}$ haloalkyl group, OR, $S(O)_nR$, or NRR' [wherein R and R' each independently represent a hydrogen atom, an alkyl group, an aryl group or the like; or R and R', taken together with the nitrogen atom to which they bond, are atoms to form an unsubstituted or substituted, 5- to 7-membered heterocycle] or the like; X represents a hydrogen atom, a $C_{1-4}$ alkyl group, a carboxyl group or the like; Y represents a hydrogen atom, a $C_{1-4}$ alkyl group or the like; for their details, the patent publication is referred to).

In addition, as other compounds having a xanthine oxidase inhibitory activity, for example, reported are biarylcarboxylic acid derivatives consisting of two aromatic rings, such as 2-phenylthiazole derivatives (Patent Reference 2 and Patent Reference 3); 3-phenylisothiazole derivatives (Patent Reference 4 and Patent Reference 5); phenylpyrazole derivatives (Patent References 6 to 8 and Non-Patent Reference 1); 2-phenyloxazole derivatives (Patent Reference 9); 2-phenylimidazole derivatives (Patent Reference 9); 2-phenylpyridine derivatives (Patent Reference 10); 2-phenylthiophene derivatives (Patent Reference 11).

The above patent publications do not disclose compounds having a structure of three aromatic rings directly bonding to each other.

On the other hand, compounds of the following general formula (III) are described, having an uricosuric effect and useful for treatment for hyperuricemia (Patent Reference 12):

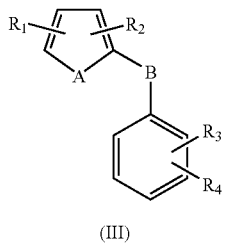

(III)

(wherein A represents an oxygen atom, a sulfur atom or a vinylene group; B represents an oxygen atom, a nitrogen atom, —(CH$_2$)$_n$— [wherein n indicates 0 or 1] or the like; R$_1$ represents a hydrogen atom, a lower alkyl group or the like; R$_2$ represents a lower alkyl group, a hydroxyl group, a lower alkoxy group, a carboxyl group or the like; R$_3$ represents a hydrogen atom, a lower alkyl group, a hydroxyl group, a lower alkoxy group, or a lower aminoalkoxy group; R$_4$ represents a nitro group, a cyano group, a halogen atom, a trifluoromethyl group, a tetrazole group, an oxadiazolone group or the like; for their details, the patent publication is referred to).

The patent publication does not concretely disclose triarylcarboxylic acid derivatives.

In addition, as compounds having a triarylcarboxylic acid structure, reported are biphenylpyridine-carboxylic acid derivatives having an antimicrobial effect (Non-Patent Reference 2); biphenylylpyrazole-carboxylic acid derivatives having an antimicrobial effect (Non-Patent Reference 3); biphenylylisothiazole-carboxylic acid derivatives having a nematocidal effect (Patent Reference 13).

However, any of Patent Reference 13 and Non-Patent References 2 and 3 does neither disclose nor suggest a xanthine oxidase inhibiting action and an uric acid synthesis inhibiting action.

Patent Reference 1: WO 92/09279
Patent Reference 2: JP-A-2002-105067
Patent Reference 3: WO 96/31211
Patent Reference 4: JP-A-57-85379
Patent Reference 5: JP-A-6-211815
Patent Reference 6: JP-A-59-95272
Patent Reference 7: WO 98/18765
Patent Reference 8: JP-A-10-310578
Patent Reference 9: JP-A-6-65210
Patent Reference 10: WO 2006/022374
Patent Reference 11: WO 2006/022375
Patent Reference 12: JP-A-2000-1431
Patent Reference 13: U.S. Pat. No. 4,539,328
Non-Patent Reference 1: Bioorganic Medicinal Chemistry Letters, 2001, Vol. 11, pp. 879-882
Non-Patent Reference 2: Pharmazie, 1999, Vol. 54, pp. 178-183
Non-Patent Reference 3: Bioorganic Medicinal Chemistry Letters, 2003, Vol. 13, pp. 2231-2234

DISCLOSURE OF THE INVENTION

Problems that the Invention is to Solve

An object of the present invention is to provide a novel and highly safe agent for treating hyperuricemia, gout, inflammatory bowel disease, diabetic nephropathy, diabetic retinopathy and the like, based on its excellent xanthine oxidase inhibiting action.

Means for Solving the Problems

The present inventors have assiduously investigated compounds having a xanthine oxidase inhibiting action and, as a result, have found that a triarylcarboxylic acid derivative of the following general formula, which is characterized by having a carboxyl group-substituted heteroaryl group and an aromatic group such as a phenyl group that are para-substituted on the benzene ring therein, and having a cyano group on the benzene ring, has a potent xanthine oxidase inhibiting action and have an excellent pharmacological effect based on it; and have further found that the derivate may be an excellent agent for treating or preventing hyperuricemia, gout, inflammatory bowel disease, diabetic nephropathy, diabetic retinopathy and the like, and thus have completed the present invention.

The compound of the present invention differs from conventional xanthine oxidase inhibitors (Patent References 1 to 11, Non-Patent Reference 1) and uricosuric agents (Patent Reference 12) in point of its structure, in that it has a basic structure of three aromatic rings directly bonding to each other. In addition, the compound of the present invention differs from the compounds described in Patent Reference 13 and Non-Patent References 2 and 3 in point of its structural characteristic, in that it requires a cyano group in the center benzene ring, and quite differs from the latter in point of its pharmacological effect.

Specifically, the present invention relates to a novel triarylcarboxylic acid derivative represented by the following general formula (I):

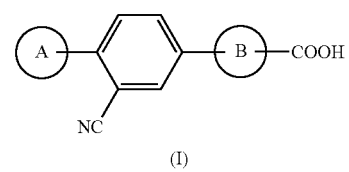

(I)

(wherein the symbols in the formula have the following meanings:

A: aryl or heteroaryl, wherein aryl and heteroaryl may be substituted with the same or different, 1 to 3 substituents selected from the following group G;

group G: halogen, —CN, —NO$_2$, lower alkyl, halogeno-lower alkyl, —O—R$^1$, —O-halogeno-lower alkyl, —O—CO—R$^1$, —O-benzyl, —O-phenyl, —NR$^2$R$^3$, —NH—CO—R$^1$, —CO$_2$—R$^1$, —CO—R$^1$, —CO—NR$^2$R$^3$, —CO-phenyl, —S—R$^1$, —SO$_2$-lower alkyl, —SO$_2$-phenyl, —NH—SO$_2$-naphthalene-NR$^2$R$^3$, phenyl, cycloalkyl, and -lower alkylene-O—R$^1$;

R$^1$: H or lower alkyl;

R$^2$ and R$^3$: same or different, each representing H or lower alkyl, wherein R$^2$ and R$^3$, taken together with the nitrogen atom to which they bond, may form a monocyclic nitrogen-containing saturated heterocycle; and B: monocyclic heteroaryl, wherein the monocyclic heteroaryl may be substituted with a group selected from lower alkyl, —OH, and halogen, and the same shall apply hereinunder).

The present invention also relates to a pharmaceutical composition comprising a triarylcarboxylic acid derivative of the general formula (I) above or a pharmaceutically acceptable salt thereof, and a pharmaceutically acceptable carrier. Preferably, the pharmaceutical composition is a xanthine oxidase inhibitor, and is an agent for preventing or treating hyperuricemia, gout, inflammatory bowel disease, diabetic nephropathy, diabetic retinopathy.

Other embodiments of the present invention include use of a triarylcarboxylic acid derivative of the general formula (I) or a pharmaceutically acceptable salt for the manufacture of a xanthine oxidase inhibitor, or an agent for preventing or treating hyperuricemia, gout, inflammatory bowel disease, diabetic nephropathy, diabetic retinopathy; and a method for preventing or treating hyperuricemia, gout, inflammatory bowel disease, diabetic nephropathy, diabetic retinopathy, which comprises administering a therapeutically-effective amount of a triarylcarboxylic acid derivative of the general formula (I) or a pharmaceutically acceptable salt thereof to a patient.

Effect of the Invention

The compound of the present invention has a potent xanthine oxidase inhibiting action. Further, the compound of the present invention has a non-nucleic acid structure, and has a triaryl structure which conventional xanthine oxidase inhibitors do not have. The compound of the present invention is free from a side effect based on inhibition of pyrimidine metabolic pathway, and is therefore advantageous in that it has a more excellent profile as compared with existing xanthine oxidase inhibitors such as allopurinol. In particular, it is useful as an agent for treating or preventing hyperuricemia, gout, inflammatory bowel disease, diabetic nephropathy, diabetic retinopathy.

BEST MODE FOR CARRYING OUT THE INVENTION

The present invention is described in detail hereinunder.

Unless otherwise specifically indicated, the term "lower" in the definition of the general formulae in this description means a linear or branched carbon chain having from 1 to 6 carbon atoms (hereinafter this is abbreviated as $C_{1-6}$). Accordingly, "lower alkyl" is $C_{1-6}$ alkyl, preferably linear alkyl such as methyl, ethyl, n-propyl and n-butyl groups; and branched alkyl such as isopropyl, isobutyl, tert-butyl and neopentyl groups. More preferred is $C_{1-4}$ alkyl; and even more preferred are methyl, ethyl, n-propyl, isopropyl and tert-butyl groups. "Lower alkylene" is $C_{1-6}$ alkylene, preferably linear alkylene such as methylene, ethylene, trimethylene and tetramethylene groups, and branched alkylene such as propylene, ethylethylene, 1,2-dimethylethylene and 1,1,2,2-tetramethylethylene groups. More preferred is $C_{1-4}$ alkylene.

"Halogen" indicates F, Cl, Br and I. Preferably, it is F. "Halogeno-lower alkyl" means a $C_{1-6}$ alkyl substituted with at least one halogen, and is preferably $C_{1-6}$ alkyl substituted with at least one F, more preferably trifluoromethyl group.

"Cycloalkyl" means a $C_{3-10}$ saturated hydrocarbon ring group, and it may have a bridge. Preferably, it is $C_{3-8}$ cycloalkyl, more preferably cyclopropyl, cyclobutyl, cyclopentyl, cyclohexyl, cycloheptyl, cyclooctyl and adamantyl groups, even more preferably cyclopentyl, cyclohexyl and cycloheptyl groups.

"Aryl" means a $C_{6-14}$ monocyclic to tricyclic aromatic hydrocarbon ring group, including a bicyclic group of a phenyl group condensed with a monocyclic oxygen-containing saturated heterocycle or with a monocyclic cycloalkyl ring. Preferably, it is phenyl, naphthyl, and phenyl condensed with a monocyclic oxygen-containing saturated heterocycle; more preferably phenyl, naphthyl and 2,3-dihydrobenzofuran-5-yl groups; even more preferably phenyl group.

"Heteroaryl" is a generic term for a 5- or 6-membered monocyclic aromatic group having from 1 to 3 hetero atoms selected from O, S and N (monocyclic heteroaryl), as well as a bicyclic or tricyclic heteroaryl to be formed through condensation of monocyclic heteroaryls or condensation of benzene ring and monocyclic heteroaryl. The monocyclic heteroaryl is preferably pyridyl, pyrrolyl, pyrazinyl, pyrimidinyl, pyridazinyl, imidazolyl, triazolyl, thienyl, furyl, thiazolyl, pyrazolyl, isothiazolyl, oxazolyl and isoxazolyl groups; more preferably thienyl, furyl, pyridyl, pyrrol-3-yl, pyrazol-4-yl groups. The bicyclic heteroaryl is preferably benzothienyl, benzofuryl, indazolyl, indolyl, benzimidazolyl, quinazolyl, quinoxalinyl, quinolyl, isoquinolyl, cinnolinyl and phthalazinyl groups; more preferably benzothienyl, benzofuryl, indolyl and indazolyl groups. The tricyclic heteroaryl is preferably carbazolyl, dibenzo[b,d]furanyl and dibenzo[b,d]thienyl groups.

In the "heteroaryl", the ring atom S may be oxidized to form an oxide or dioxide, or N may be oxidized to form an oxide.

The monocyclic heteroaryl for the ring group A is preferably thienyl, furyl, pyrrolyl, pyrazolyl, imidazolyl, 1,2,3-triazolyl, 1,3,4-triazolyl, pyridyl, pyrimidinyl, benzothienyl, benzofuryl, benzopyrazolyl, 1,3-benzodioxolyl, indolyl, quinolyl, fluorenyl, naphthalenyl, quinoxalinyl, dibenzo[b,d]furanyl and dibenzo[b,d]thienyl groups, more preferably thienyl, pyridyl, furyl, benzothienyl and benzofuryl.

The monocyclic heteroaryl for the ring group B is preferably pyridyl, pyrrolyl, pyrazinyl, pyrimidinyl, pyridazinyl, imidazolyl, triazolyl, thienyl, furyl, thiazolyl, pyrazolyl, isothiazolyl, oxazolyl and isoxazolyl groups, more preferably pyridyl, thienyl, thiazolyl, isothiazolyl and pyrazolyl groups. The above "monocyclic heteroaryl for the ring group B" is described as a nomenclature for a monovalent group for convenience' sake; however, the ring group is a divalent group that bonds to the benzene ring and the carboxyl group.

"Monocyclic oxygen-containing saturated heterocycle" is a 5- to 7-membered saturated monocyclic heterocycle containing one or two O atoms, preferably tetrahydrofuran, 1,3-dioxolan and 1,4-dioxepine rings.

"Monocyclic nitrogen-containing saturated heterocycle" indicates a 5- to 8-membered, saturated or partially unsaturated monocyclic heterocycle containing one N atom and optionally further containing one hetero atom of N, S and O. Preferably, it is pyrrolidine, piperidine, piperazine, azepane, diazepane, azocane, morpholine, thiomorpholine and tetrahydropyridine ring. More preferably, it is pyrrolidine, piperidine, azepane and morpholine rings.

In the above "monocyclic nitrogen-containing saturated heterocycle", the ring atom S may be oxidized to form an oxide or a dioxide, or N may be oxidized to form an oxide.

Of the compound of formula (I) of the present invention, preferred embodiments are the following compounds and their salts.

1) Compounds where A is a cyclic group selected from phenyl, naphthyl, thienyl, pyridyl, furyl, benzothienyl, benzofuryl and 2,3-dihydrobenzofuran-5-yl and optionally substituted with substituent(s) of the group G.

2) More preferably, compounds where A is phenyl optionally substituted with substituent(s) of the group G.

3) More preferably, compounds where the benzene ring and the carboxyl group on the ring group B bond to the ring group B at the other positions than the positions adjacent to each other.

4) More preferably, compounds of the above 1) where B is a divalent group represented by the following formula:

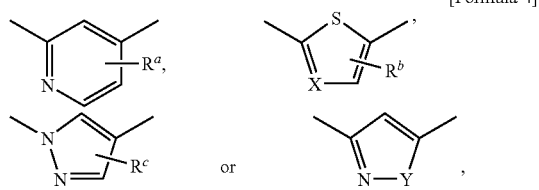

[Formula 4]

(wherein the symbols in the formula have the following meanings:

X: CH or N,

Y: O, S or $NR^d$, $R^a$, $R^b$ and $R^c$: H or methyl, and $R^d$: H or methyl, and the same shall apply hereinunder.)

5) More preferably, compounds of the above 4) where B is a ring group selected from pyridine, thiophene, thiazole, isothiazole and pyrazole rings.

The substituents of the group G are preferably halogen, —CN, lower alkyl, halogeno-lower alkyl, —O—$R^1$, —O-halogeno-lower alkyl, —S—$R^1$, —$NR^2R^3$, —$CO_2$—$R^1$, and -lower alkylene-O—$R^1$.

The substituents of $R^a$ to $R^c$ are preferably H and methyl.

At least one compound selected from the group mentioned below is especially preferred.

2-(2-Cyanobiphenyl-4-yl)isonicotinic acid, 2-(2-cyano-4'-methoxybiphenyl-4-yl)isonicotinic acid, 2-(4'-chloro-2-cyanobiphenyl-4-yl)isonicotinic acid, 5-(2-cyanobiphenyl-4-yl)thiophene-2-carboxylic acid, 2-(2-cyano-4'-methylbiphenyl-4-yl)-4-methyl-1,3-thiazole-5-carboxylic acid, 2-(2-cyanobiphenyl-4-yl)-4-methyl-1,3-thiazole-5-carboxylic acid, 2-[2-cyano-4'-(trifluoromethoxy)biphenyl-4-yl]-4-methyl-1,3-thiazole-5-carboxylic acid, 2-(2-cyano-4'-methoxybiphenyl-4-yl)-4-methyl-1,3-thiazole-5-carboxylic acid, 2-(2-cyano-3'-methoxybiphenyl-4-yl)-4-methyl-1,3-thiazole-5-carboxylic acid, 2-(2-cyano-3'-methylbiphenyl-4-yl)-4-methyl-1,3-thiazole-5-carboxylic acid, 1-(2-cyanobiphenyl-4-yl)-1H-pyrazole-4-carboxylic acid, 1-(2-cyano-4'-methylbiphenyl-4-yl)-1H-pyrazole-4-carboxylic acid, 1-(2-cyano-4'-methoxybiphenyl-4-yl)-1H-pyrazole-4-carboxylic acid, 2-(2-cyanobiphenyl-4-yl)-1,3-thiazole-5-carboxylic acid, 3-(2-cyanobiphenyl-4-yl)isothiazole-5-carboxylic acid, 3-(4'-tert-butyl-2-cyanobiphenyl-4-yl)isothiazole-5-carboxylic acid, and 3-(2-cyanobiphenyl-4-yl)-1-methyl-1H-pyrazole-5-carboxylic acid.

Depending on the type of the substituent therein, the compound of the present invention may include tautomeric isomers and optical isomers; and the present invention encompasses mixtures of these isomers, and isolated isomers.

Further, the present invention includes "pharmaceutically acceptable prodrugs" of compounds of formula (I). The "pharmaceutically acceptable prodrug" is a compound having a group capable of being converted into $CO_2H$, $NH_2$, OH or the like through solvolysis or under a physiological condition, thereby giving a compound (I) of the present invention. The group to form the prodrugs includes those described in Prog. Med., 5, 2157-2161 (1985), and those described in "Development of Medicines" (Hirokawa Publishing, 1990), Vol. 7, Molecular Design, pp. 163-198.

The salts of compound (I) of the present invention are pharmaceutically acceptable salts, concretely including acid-addition salts with an inorganic acid such as hydrochloric acid, hydrobromic acid, hydroiodic acid, sulfuric acid, nitric acid, phosphoric acid; or an organic acid such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, aspartic acid, glutamic acid. Depending on the type of the substituent therein, the compound (I) may form salts with a base, including, for example, salts with an inorganic base that contains a metal such as sodium, potassium, magnesium, calcium, aluminium or lithium, or with an inorganic base such as methylamine, ethylamine, ethanolamine, lysine or ornithine; and ammonium salts.

Further, the compound (I) and its salts of the present invention include various hydrates, solvates and polymorphic crystal substances.

(Production Methods)

Taking advantage of the characteristics based on the basic structure thereof or on the type of the substituent therein, the compound of the present invention may be produced according to various known production methods. Depending on the type thereof, the functional group in the starting compounds or intermediates may be protected with a protective group or may be modified into a group capable of being readily convertible into the functional group, and this may be technically effective in producing the compounds. The functional group includes, for example, an amino group, a hydroxyl group and a carboxyl group. Their protective groups are described, for example, in Greene (T. W. Greene) & Wuts (P. G. M. Wuts)'s "Protective Groups in Organic Synthesis, (3rd Ed., 1999)". Depending on the reaction condition, these may be used suitably. According to the method, after protective group introduction, the reaction is performed, then the protective group may be optionally removed or the modified group may be converted into the desired group to obtain the intended compound.

Prodrugs of compound (I) or its salt may be produced by introducing a specific group into the starting compounds or intermediates, like the above-mentioned protective group thereinto, or by further processing the obtained compound (I). The reaction may be attained in any method known to those skilled in the art, including ordinary esterification, amidation, acylation, etc.

Production Method 1:

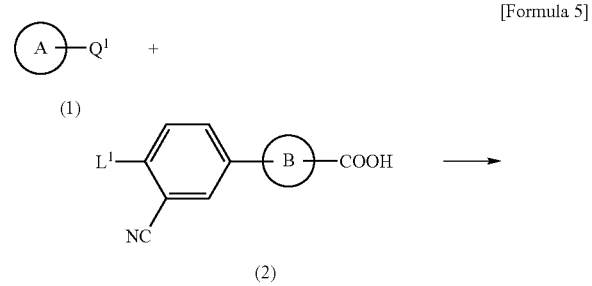

[Formula 5]

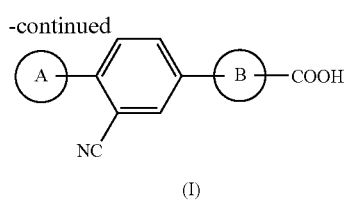

(I)

(In the formula, $Q^1$ represents —B(OH)$_2$ or —B(OR$^4$)OR$^5$, L$^1$ represents a leaving group. In this, R$^4$ and R$^5$ are the same or different, each representing lower alkyl; or R$^4$ and R$^5$, taken together, may form lower alkylene. The same shall apply hereinunder.) This production method is a method for producing a compound (I) of the present invention by coupling a compound (1) and a compound (2).

The leaving group represented by L$^1$ includes halogen, methanesulfonyloxy, p-toluenesulfonyloxy, trifluoromethanesulfonyloxy groups. The reaction may be performed by reacting the compounds (1) and (2) in an equivalent ratio, or in such a manner that any one of the two is excessive, in a solvent inert to the reaction, in the presence of a base and a palladium catalyst, at room temperature or by heating until reflux, generally for 0.5 hours to 5 days. Preferably, the reaction is effected in an inert gas atmosphere. It may be favorable to use microwave irradiation in heating in the reaction. Non-limiting example of the solvent used here includes aromatic hydrocarbons such as benzene, toluene, xylene; ethers such as diethyl ether, tetrahydrofuran (THF), 1,4-dioxane, 1,2-dimethoxyethane, 1,2-diethoxyethane; halogenohydrocarbons such as dichloromethane, 1,2-dichloroethane, chloroform; alcohols such as methanol, ethanol, 2-propanol, butanol; N,N-dimethylformamide (DMF), N-methylpyrrolidone (NMP), dimethylsulfoxide (DMSO), water and their mixed solvents. The base is preferably an inorganic base such as sodium carbonate, potassium carbonate, sodium hydroxide, potassium hydroxide, sodium ethoxide, sodium methoxide. Other bases such as potassium fluoride and cesium fluoride are also usable herein. In this case, the reaction is preferably effected in an aprotic solvent. The palladium catalyst is preferably tetrakis(triphenylphosphine)palladium, dichlorobis(triphenylphosphine)palladium, palladium chloride-1,1'-bis(diphenylphosphino)ferrocene.

Production Method 2:

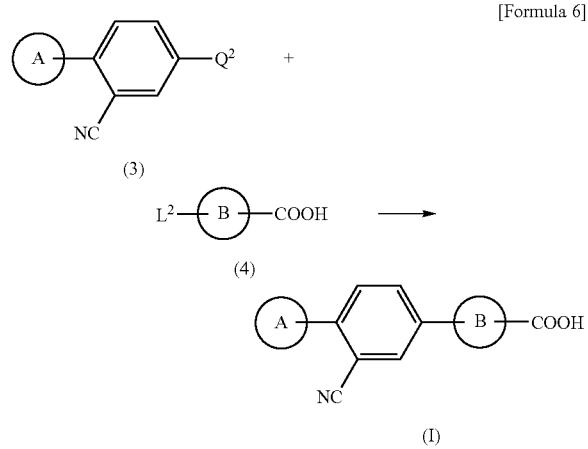

[Formula 6]

(In the formula, $Q^2$ is the same group as the previously described $Q^1$; $L^2$ is the same group as the previously described $L^1$. The same shall apply hereinunder.)

This production method is a method for producing a compound (I) of the present invention by coupling a compound (3) and a compound (4). The condition for the above production method 1 may apply to this reaction.

Production Method 3:

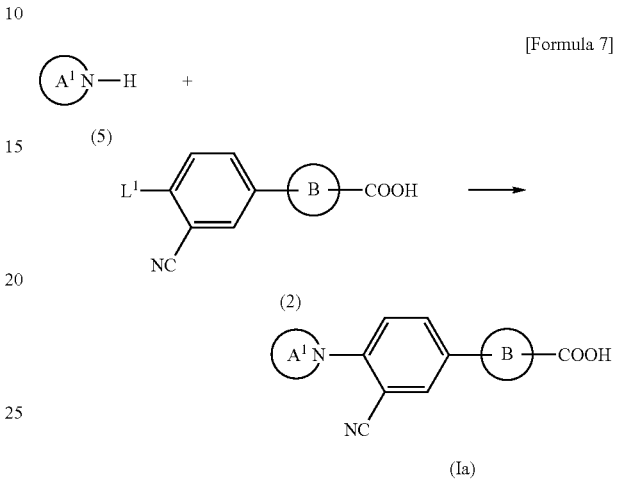

[Formula 7]

(In the formula, A$^1$ represents a monocyclic to tricyclic heteroaryl group within the ring group A in the previously described formula (I), and this has a nitrogen atom as the ring-constituting atom and bonds to the benzene ring via the nitrogen atom.)

This production method is a method for producing a compound (Ia) of the present invention by subjecting a compound (5) and a compound (2) to substitution reaction.

This reaction may be effected by reacting a compound (5) and a compound (2) in an equivalent ratio or in such a manner that the compound (5) is excessive, in a solvent inert to the reaction, at room temperature or by heating until reflux, generally for 0.1 hours to 5 days. Non-limiting example of the solvent used here includes, for example, the above-mentioned aromatic hydrocarbons, ethers, halogenohydrocarbons, DMF, NMP, DMSO and their mixed solvents. As the case may be, the reaction may be favorably effected in the presence of a base or a phase transfer catalyst. The base in this case includes organic bases such as triethylamine, diisopropylethylamine (DIPEA), 1,8-diazabicyclo[5.4.0]-7-undecene (DBU); and inorganic bases such as sodium carbonate, potassium carbonate, cesium carbonate, sodium hydride, potassium tert-butoxide. The phase transfer catalyst includes tetra-n-butylammonium chloride, tetra-n-butylammonium bromide, 18-crown-6.

In the reaction of the production method 1, the production method 2 and the production method 3, it is desirable that the CO$_2$H group is previously protected with a protective group, and after the intended reaction, the protective group is removed. For the selection of the protective group and for the condition for the protection and the removal, referred to are the methods described in the above-mentioned "Protective Groups in Organic Synthesis, 3rd Ed., 1999".

Other Production Methods:

Compounds of the present invention having various functional groups may be produced according to method obvious to those skilled in the art or known methods, or according to their modifications. For example, the compounds of the present invention obtained in the above-mentioned production methods may be subjected to substituent modification, thereby producing desired compounds of the present invention. Typical reactions are mentioned below.

(1) Amidation and Esterification:

Of the compounds (I) of the present invention, those having an amido group or those having an ester group may be produced, starting from the corresponding compound that has a hydroxyl group or an amino group and reacting it with a carboxylic acid or its reactive derivative. For the reaction, for example, referred to are the methods described in "Courses in Experimental Chemistry" by the Chemical Society of Japan, 4th Ed., Vol. 22, 1992 (Maruzen).

(2) Oxidation:

Of the compounds (I) of the present invention, those having a sulfonyl group or a sulfenyl group may be produced through oxidation of the corresponding compound having a sulfido group. For it, for example, referred to are the methods described in "Courses in Experimental Chemistry" by the Chemical Society of Japan, 4th Ed., Vol. 22, 1992 (Maruzen).

(3) Alkylation:

Of the compounds (I) of the present invention, those having a lower alkoxy group or a lower alkylamino group may be produced through alkylation of the corresponding compound having a hydroxyl group or an amino group. The condition for the reaction may be the same as that for the production method 3.

Production Methods for Staring Compounds:

(In the formula, $L^3$ represents a sulfonyloxy group such as a methanesulfonyloxy, p-toluenesulfonyloxy, or trifluoromethanesulfonyloxy group; Hal represents halogen; and the same shall apply hereinunder.)

<

The starting compound (2a) may be produced according the above-mentioned reaction scheme.

In the above reaction scheme, the boronation may be effected according to the method described in "Chem. Rev. 95, 2547-2483 (1995)", "J. Org. Chem. 67, 5394-5397 (2002)", "J. Org. Chem. 65, 164-168 (2000)" or "J. Org. Chem. 60, 7508-7510 (1995)". The hydrolysis may be effected according to the methods described in "Chem. Rev. 95, 2547-2483 (1995)" or "J. Org. Chem. 67, 5394-5397 (2002)". The coupling reaction may be effected under the same condition as that for the above-mentioned production method 1. The sulfonyl esterification may be effected according to ordinary methods. In the above reaction scheme, it is desirable that the phenolic hydroxyl group in the compound (6) and the carboxyl group in the compound (4) are protected with a protective group. For the protective group and the condition for protection and deprotection, referred to are the methods described in the above-mentioned "Protective Groups in Organic Synthesis, 3rd Ed., 1992".

[Formula 8]

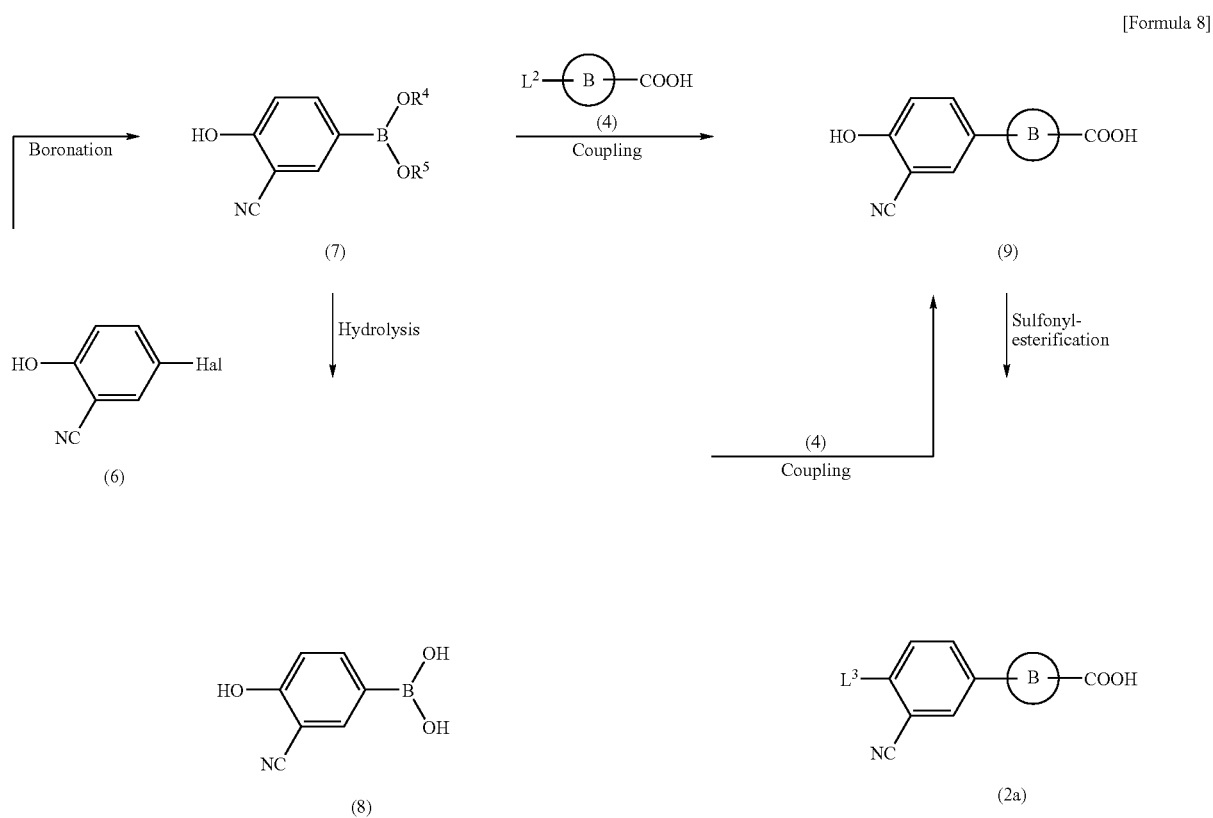

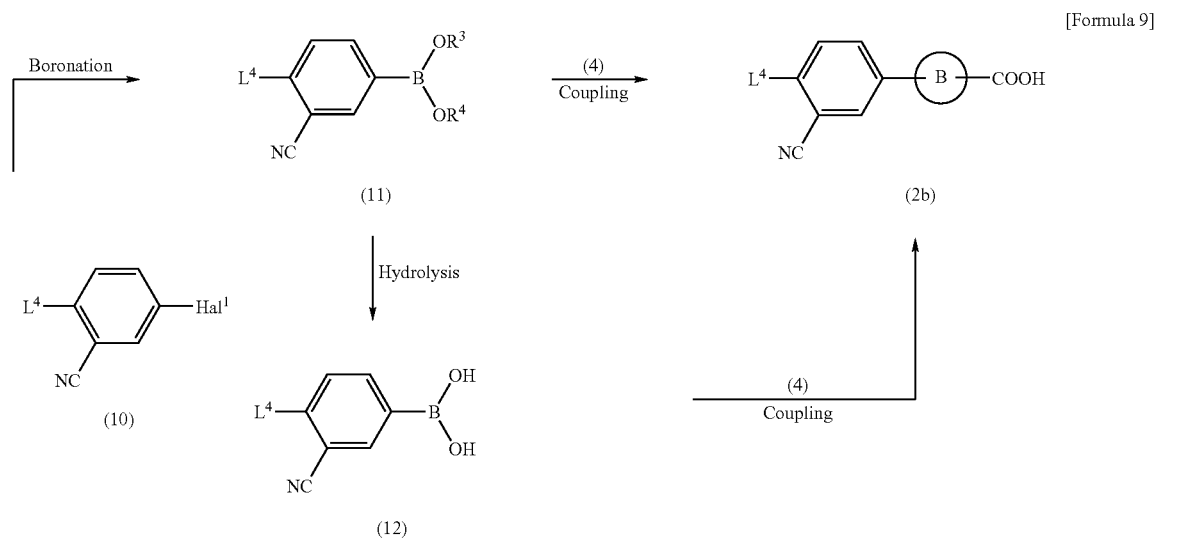

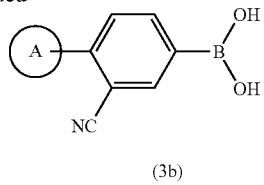

(In the formula, $L^4$ represents F or Cl; Hal1 represents Br or I; and the same shall apply hereinunder.)

The starting compound (2b) may be produced according to the above-mentioned reaction scheme. In this, the condition for the boronation and the hydrolysis may be the same as that for the production method for the starting compounds (7) and (8); and the condition for the coupling reaction may be the same as that for the above-mentioned production method 1.

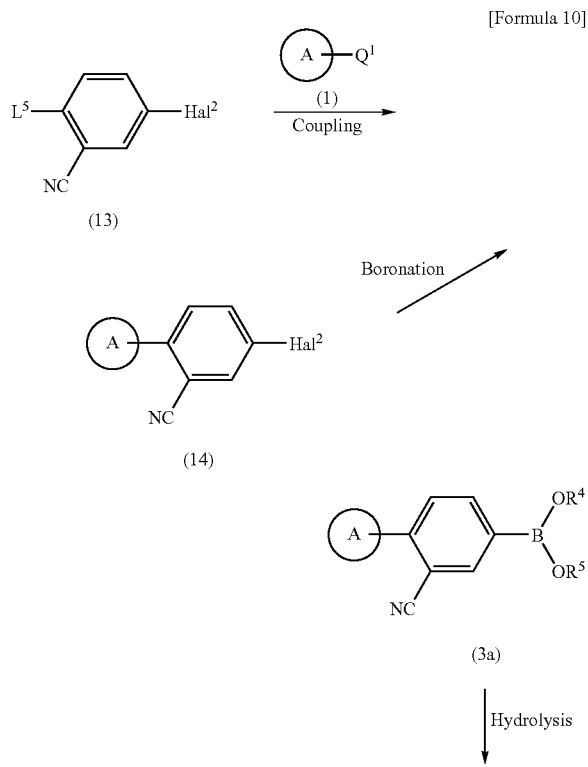

(In the formula, $L^5$ represents I or a trifluoromethanesulfonyloxy group; Hal2 represents Br or Cl; and the same shall apply hereinunder.)

The starting compounds (3a) and (3b) may be produced according to the above-mentioned reaction scheme. In the reaction scheme, the condition for the coupling reaction may be the same as that for the above-mentioned production method 1; and the condition for the boronation and the hydrolysis may be the same as that for the production method for the starting compounds (7) and (8).

Thus produced, the compound (I) may be isolated and purified directly as it is in the form of a free compound, or after formed into its salt according to ordinary salt formation. The isolation and purification may be attained through ordinary chemical treatment of extraction, concentration, distillation, crystallization, filtration, recrystallization and various chromatography.

Various isomers may be isolated by separating them according to ordinary methods based on the difference between the isomers in the physical or chemical properties thereof. For example, optical isomers may be separated and purified according to a method of leading a racemic compound into a diastereomer salt with an optically-active organic acid (e.g., tartaric acid) and then subjecting it into fractionating crystallization, or a method of column chromatography using a chiral filler. In addition, optically-active compounds may be produced, starting from a suitable optically-active compound. Diastereomer mixtures may be separated through fractionating crystallization or chromatography.

(Test Methods)

The effect of the compounds of the present invention was confirmed according to the pharmacological tests mentioned below.

1. Xanthine Oxidase Inhibiting Activity:

(1) Preparation of Test Compound:

A test compound was dissolved in DMSO (by Nacalai) to have a concentration of 10 mM, and then just before use, its concentration was adjusted to a desired one.

(2) Measurement Method:

The xanthine oxidase inhibitory activity of the compound of the present invention was evaluated according to a partly modified method of a method described in a reference "Free Radic. Biol. Med. 6, 607-615, 1992". Concretely, xanthine oxidase (derived from butter milk, by Sigma) was mixed with 50 mM phosphate buffer to be 0.03 units/ml, and applied to a 96-well plate in an amount of 50 l/well. The test compound diluted to have a final concentration was added to the plate in an amount of 2 μl/well, and processed at room temperature for 20 minutes. Pterin (by Sigma) was added to it to have a final concentration of 5 μM in an amount of 50 μl/well, and reacted at room temperature for 10 minutes. Under a condition of excitation at 345 nm and emission at 390 μm (pterin is oxidized by xanthine oxidase to give isoxanthopterin, and under the condition it emits light), the sample was analyzed using a microplate reader sapphire (by Tacan).

The light emission by isoxanthopterin in the presence or absence of xanthine oxidase was defined as 0% inhibition and 100% inhibition, respectively, and the concentration ($IC_{50}$) of the test compound for 50% inhibition was computed.

The compounds of the present invention had good xanthine oxidase inhibitory activity. For example, the compound of Example 94 had $IC_{50}$ of 0.5 nM; the compound of Example 129 had $IC_{50}$ of 0.9 nM; the compound of Example 140 had $IC_{50}$ of 1.4 nM. The compounds of Examples 1 to 5, 7 to 9, 12 to 14, 17, 19, 21, 29, to 41, 43, 46, 49, 58, 63, 68, 82, 84, 102, 105, 107, 123 to 128, 136 to 138, 146, 152 and 153 all had $IC_{50}$ of 10 nM or less.

The above test confirmed that the compounds of the present invention have potent xanthine oxidase inhibitory activity.

2. Hypouricemic Effect (Normal Mouse):

A test compound suspended in 0.5% methyl cellulose liquid was given to an ICR mouse through forced oral administration using an oral probe. 2 hours or 6 hours after the administration, or with some compounds, further 24 hours after it, the blood was collected from the mouse through its abdominal aorta, and the serum was separated from it. The serum uric acid level was measured according to an uricase method using an absorption spectrometer (SPECTRA MAX 190, by Molecular Device) and using an uric acid measurement kit (uric acid C-test Wako, by Wako Pure Chemicals), and the percentage of hypouricemic effect was obtained according to the following formula:

Percentage of hypouricemic effect (%)=(Uric acid level of control animal−uric acid level of test compound-administered animal)×100/uric acid level of control animal.

This test confirmed the excellent hypouricemic effect of the compounds of the present invention. For example, the compounds of Examples 1 and 12 showed an uric acid depression percentage of 70% or more in 2 hours after 1 mg/kg oral administration. In addition, the compounds has long-acting effect, for example, the compounds of Examples 12 and 13 kept their uric acid lowering percentage of 50% or more even in 24 hours after the administration thereof.

From the above result, it is obvious that the compounds of the present invention have a potent and long-acting hypouricemic effect.

3. Hypouricemic Effect (Rat Oxonate-Induced High Uric Acid Model):

(A) For evaluating the serum uric acid level depressing capability of the compounds of the present invention, the following test was carried out using an oxonate-induced high uric acid model.

A 0.5% methyl cellulose liquid (normal group, control group) or a test compound suspended in 0.5% methyl cellulose (compound-administered group) was orally administered to 5 or 6-week-age male Wistar rats. One hour before blood collection, saline (normal group), or 250 mg/kg of potassium oxonate suspended in saline (control group, compound-administered group) was subcutaneously administered to the rats. 2 hours or 18 hours after the compound or methyl cellulose liquid administration, the blood was collected from each rat. The serum was separated from the collected blood, and the serum uric acid level was measured according to a phosphorus tungstate method (Am. J. Clin. Pathol., 28, 152-, 1957).

This test confirmed the excellent hypouricemic effect of the compounds of the present invention. For example, $ED_{50}$ of the compound of Example 136 was 0.2 mg/kg in 2 hours after oral administration (for this, the serum uric acid level of the normal group was defined as 100% inhibition and the serum uric acid level of the control group was as 0% inhibition). In addition, $ED_{50}$ of the compounds of Examples 1, 68, 123, 124, 127, 137, 140 and 146 was all less than 1 mg/kg, as evaluated in 2 hours after oral administration. Further, even in evaluation in 18 hours after oral administration, the compounds of the present invention still showed the potent activity.

(B) Further, the excellent hypouricemic effect of the compounds of the present invention can also be confirmed by the following test method which is a modification of the above test method (A).

Wistar rats were fed with feed prepared by adding 2.5% potassium oxonate (by Tokyo Kasei) to CE-2 (Nippon Clea) thereby producing chronic high uric acid models (see Metabolism, 1994 January; 43(1): 123-8). A test compound suspended in 0.5% methyl cellulose, or 0.5% methyl cellulose liquid (control group) was orally administered to them once a day; and after the administration on day 3, the blood was periodically collected from them. According to the phosphotungstic acid method, the serum uric acid level was computed from the collected blood. The test confirmed the excellent hypouricemic effect of the compounds of the present invention.

In the above test method (B), the serum blood level at the time of blood collection may be increased over the saturated uric acid concentration (7 mg/dl) by intraperitoneal administration of 1 mg/kg/10 ml isoproterenol at 1 hour before each blood collection. The present models confirmed the excellent hypouricemic effect of the compounds of the present invention.

As in the above, the disease models showed the potent and long-acting hypouricemic effect of the compounds of the present invention.

Further, the effectiveness of the compounds of the present invention for inflammatory bowel disease may be evaluated according to the test methods mentioned below.

4. Acetic Acid-Induced Enteritis Suppressing Action:

One ml of 4% acetic acid was rectally administered to Wistar rats kept away from feeding for 2 days. In place of acetic acid, 1 ml of saline was administered as a normal group. Next, a test compound suspended in 0.5% methyl cellulose liquid (compound-administered group) or 0.5% methyl cellulose liquid (control group) was orally administered to the 4% acetic acid-administered group, while 0.5% methyl cellulose liquid was to the normal group, each once a day for 4 days. The part of from 2 to 7 cm from the anus side of the large intestine was cut out, then the feces were removed from it with tweezers, and it was washed and the tissue weight was measured.

The tissue weight increase inhibition of the test compound was computed according to the following method.

Tissue Weight Increase Inhibition (%)=100−{(tissue weight of the compound-administered group−tissue weight of the normal group)/(tissue weight of the control group−tissue weight of the normal group)×100}.

The compounds of the present invention showed a significant tissue weight inhibition. The result confirmed the effectiveness of the compounds of the present invention for inflammatory bowel disease.

5. Diabetic Retinopathy Model:

The effectiveness of the compounds of the present invention for diabetic retinopathy may be evaluated according to the method described in European Journal of Pharmacology 458 (2003) 283-289 (in which the test animals are 10-week age male Wistar rats).

As described in the above, it has been confirmed that the compounds of the present invention have potent xanthine oxidase inhibition and show excellent disease-modifying effects in animal tests. In addition, since the compounds of the present invention have metabolic stability, and have a long-acting hypouricemic effect, they are superior to conventional xanthine oxidase inhibitors. Accordingly, the compounds of the present invention are expected as an agent for treating or preventing hyperuricemia, gout, uric urolithiasis, hyperuricemia-accompanied nephropathy, inflammatory bowel disease (ulcerative colitis, Crohn's disease), diabetic nephropathy, diabetic retinopathy, organ dysfunction in organ transplantation or ischemic reperfusion, tumor lysis syndrome, cardiac failure, cardiovascular disorder, especially for hyperuricemia, gout, inflammatory bowel disease, diabetic nephropathy, diabetic retinopathy.

Further, the compounds of the present invention have a non-nucleic acid structure, and are free from side effects based on pyrimidine metabolic pathway disorder, and are therefore promising as safe medicines.

A pharmaceutical composition containing, as the active ingredient thereof, a compound (I) or its salt of the present invention may be prepared, using a carrier and a vehicle and any other additives generally used for preparation of pharmaceutical compositions.

The administration may be in any route of oral administration with tablets, pills, capsules, granules, powders, liquids; or non-oral administration with injections such as intravenous or intramuscular injections, suppositories, endermic agents, nasal agents or inhalants. The dose of the compound of the present invention may be suitably determined for each compound, depending on the condition, and the age and the sex of the patient to whom the compound is applied. In general, it may be from 0.001 to 100 mg/kg-adult/day or so for oral administration, and this may be administered all at once or in 2 to 4 times in a day. In intravenous administration taken depending on the pathologic condition of a case, the dose may be generally within a range of from 0.0001 to 10 mg/kg-adult/day, and this may be administered all at once or in a few times in a day. In inhalation, in general, the dose may be from 0.0001 to 1 mg/kg-adult/day, and this may be administered all at once or in a few times in a day.

The solid composition for oral administration may be tablets, powders or granules. In the solid composition, one or more active substances may be mixed with at least one inert vehicle, such as lactose, mannitol, glucose, hydroxypropyl cellulose, microcrystalline cellulose, starch, polyvinylpyrrolidone, magnesium metasilicate aluminate. According to an ordinary manner, the composition may contain any other additive, for example, lubricant such as magnesium silicate, disintegrator such as calcium cellulose glycolate, dissolution promoter. The tablets and pills may be coated with sugar or with gastric-coating or enteric-coating film.

The liquid composition for oral administration includes pharmaceutically acceptable emulsion, solution, suspension, syrup and elixir, and contains an ordinary inert solvent such as pure water, ethanol. The composition may contain any other additive than such an inert solvent, for example, auxiliary agent such as solubilizer, wetting agent, suspending agent, as well as sweetener, flavoring, fragrance, and preservative.

The injection for non-oral administration includes germ-free water-base or waterless solution, suspension and emulsion. The water-base solvent includes, for example, distilled water for injection and physiological brine. The waterless solvent includes, for example, propylene glycol, polyethylene glycol, vegetable oil such as olive oil, alcohols such as ethyl alcohols, Polysorbate 80 (name by Pharmacopeia). The composition may further contain isotonizer, preservative, wetting agent, emulsifier, dispersant, stabilizer, dissolution promoter. These may be sterilized through filtration through a bacteria-trapping filter, or by addition of germicide, or through irradiation with light. As the case may be, a germ-free solid composition may be prepared, and it may be dissolved in germ-free water or germ-free solvent for injection to give the intended liquid composition before use.

The intramucosal composition such as inhalant and nasal agent may be solid, liquid or semi-solid, and it may be produced according to a known method. For example, vehicles such as lactose and starch, and further pH-controlling agent, preservative, surfactant, lubricant, stabilizer and thickener may be suitably added. For its administration, usable is any suitable device for inhalation or insufflation. For example, using a known device or spray such as a metered dose inhalation device, the compound may be administered singly, or as a formulated mixture powder thereof or as a solution or suspension thereof combined with a pharmaceutically acceptable carrier. The dry powder inhalator may be for single-dose administration or multi-dose administration, for which dry powder or powder-containing capsules may be used. As the case may be, it may be in the form of a pressure aerosol spray using a suitable propellant, for example, a favorable vapor such as chlorofluoroalkane, hydrofluoroalkane or carbon dioxide.

In producing suppositories, a low-melting-point wax such as a fatty acid glyceride mixture or cocoa butter is melted, an active ingredient is added thereto, followed by stirring for uniform dispersion. Next, this is cast into a suitable mold and cooled and solidified. Liquid preparations include solution, suspension, holding enema and emulsion, for example, water or aqueous propylene glycol solution.

EXAMPLES

The compounds of the present invention are described more concretely with reference to the following Examples. Production methods for starting compounds are described as Reference Examples. The production methods for the compounds of the present invention are not limited to only the production methods of the concrete Examples shown below, and the compounds may also be produced according to their combinations or known methods.

The abbreviations in Reference Examples, Examples and Tables shown below are as follows:
Ex: Number of Example
REx: Number of Reference Example
Dat: Physicochemical data (FA: FAB-MS (M+H)$^+$, FN: FAB-MS (M−H)$^-$, ES: ESI-MS (M+H)$^+$, EI: EI-MS (M$^+$), AP: API-ES-MS (M+H)$^+$, APN: API-ES-MS (M−H)$^-$, [the compound with (Na) after its mass-spectrometric data means that its Na salt or Na adduct gave the data; and the compound with (G-2W) after its mass-spectrometric data means that its glycerin adduct didehydrate gave the data], NMR: δ (ppm) of characteristic peaks in $^1$H NMR in DMSO-d$_6$, NMRC: δ (ppm) of characteristic peaks in $^1$H NMR in CDCl$_3$)
Anal: Elementary analysis
Calc. calculated data
Found: found data
H: Retention time (min) in HPLC under the following condition, [HPLC condition: column, Wakosil-II 5C18AR 5 μm, 2.0×30 mm; detection wavelength, 254 nm; measuring temperature, 35.0° C.; solvent, started in aqueous 5 mM trifluoroacetic acid solution/MeOH=9/1, and the ratio was changed to 0/10 within 4 minutes, and afterwards, the sample was eluted at 0/10 for 0.5 minutes, the flow rate was 1.2 ml/min]
Str: Structural formula
Syn: Production method (Numeral means the number of Example as referred to in producing the compound in the same manner)
Sal: Salt (the compound with no mark is a free base, the compound designated by 0.3HCl means that it is a mixture of monohydrochloride and free base in a molar ratio of 0.3/0.7]
Me: Methyl
Et: Ethyl
iPro: 2-Propyl
nBu: N-butyl
iBu: Isobutyl
tBu: tert-butyl
cHex: Cyclohexyl
Bn: Benzyl
Ph: Phenyl
3Py: 3-Pyridyl
4Py: 4-Pyridyl
2Thie: 2-Thienyl
3Thie: 3-Thienyl
2Fur: 2-Furyl
3Fur: 3-Furyl
1Naph: 1-Naphthyl
2Naph: 2-Naphthyl
Ac: Acetyl
Tf: Trifluoromethanesulfonyl
A substituted phenyl group is represented as "numeral indicating the substituent position-abbreviation of the substituent-Ph" in the Tables. "di" before the substituent means that the group has two substituents. For example, 4-MeO-3, 5-diMe-Ph- means 4-methoxy-3,5-dimethylphenyl group.

In the column "Syn" relative to the production method in the Tables below, the same Reference Number is given to the compounds of which the salt forms differ but which were produced through the same type of reaction. Interconversion between a free base and its salt is a technical common sense of those skilled in the art.

Reference Example 1

5-Bromo-2-hydroxybenzonitrile, benzyl bromide and potassium carbonate were reacted in DMF at room temperature to obtain 2-(benzyloxy)-5-bromobenzonitrile. EI: 287, 289.

Reference Example 2

2-(Benzyloxy)-5-bromobenzonitrile and triisopropyl borate were dissolved in a mixed solvent of THF and toluene, and at −78° C., an n-butyllithium/hexane solution was dropwise added. This was heated up to room temperature, and 1 M hydrochloric acid was added to the reaction mixture, followed by stirring to obtain [4-(benzyloxy)-3-cyanophenyl] boric acid. ES: 254.

Reference Example 3

[4-(Benzyloxy)-3-cyanophenyl]boric acid and methyl 2-chloroisonicotinate were dissolved in a mixture liquid of toluene and an aqueous 2 M sodium carbonate solution, and in the presence of tetrakis(triphenylphosphine)palladium, the mixture was stirred under heating in an argon atmosphere at 10° C. to obtain methyl 2-[4-(benzyloxy)-3-cyanophenyl] isonicotinate. F: 345.

Reference Example 4

Methyl 2-[4-(benzyloxy)-3-cyanophenyl]isonicotinate and pentamethylbenzene were heated under reflux in trifluoroacetic acid to obtain methyl 2-(3-cyano-4-hydroxyphenyl) isonicotinate. F: 255.

Reference Example 5

A 4M HCl/1,4-dioxane solution was added to a DMF solution of 4-(benzyloxy)isophthalonitrile and thioacetamide, followed by stirring at 60° C. to obtain 4-(benzyloxy)-3-cyanobenzenecarbothioamide. AP: 291 (Na).

Reference Example 6

4-(Benzyloxy)-3-cyanobenzenecarbothioamide and ethyl 2-chloroacetacetate were stirred in ethanol at 75° C. to obtain ethyl 2-[4-(benzyloxy)-3-cyanophenyl]-4-methyl-1,3-thiazole-5-carboxylate. AP: 401(Na).

Reference Example 7

4-(Benzyloxy)-3-cyanobenzenecarbothioamide and methyl 2-chloro-3-oxopropionate were heated under reflux in 1-butanol in the presence of Molecular Sieves 4A to obtain methyl 2-[4-(benzyloxy)-3-cyanophenyl]-1,3-thiazole-5-carboxylate. AP: 373(Na).

Reference Example 8

Ethyl 2-[4-(benzyloxy)-3-cyanophenyl]-4-methyl-1,3-thiazole-5-carboxylate was suspended in a mixture of THF and ethanol, then palladium-carbon was added thereto, and the mixture was stirred under a hydrogen atmosphere at room temperature to obtain ethyl 2-(3-cyano-4-hydroxyphenyl)-4-methyl-1,3-thiazole-5-carboxylate. APN: 287.

Reference Example 9

Methyl 2-(3-cyano-4-hydroxyphenyl)isonicotinate and trifluoromethanesulfonic anhydride were reacted in dichloromethane at 0° C. in the presence of DIPEA to obtain methyl 2-(3-cyano-4-{[(trifluoromethyl)sulfonyl]oxy}phenyl)isonicotinate. F: 387.

Reference Example 10

Cesium fluoride and tetrakis(triphenylphosphine)palladium were added to a 1,2-dimethoxyethane solution of (3-cyano-4-fluorophenyl)boric acid and methyl 2-chloroisonicotinate, and the mixture was heated under reflux in an argon atmosphere to obtain methyl 2-(3-cyano-4-fluorophenyl)isonicotinate. F: 257.

Reference Example 11

5-Bromo-2-iodobenzonitrile and 3-pyridylboric acid were dissolved in a mixture solution of aqueous 2 M sodium carbonate solution and toluene, then tetrakis(triphenylphosphine)palladium was added thereto, and the mixture was heated, stirred with heating in an argon atmosphere at 100° C. for 3 days to obtain 5-bromo-2-pyridin-3-ylbenzonitrile. EI: 258, 260.

Reference Example 12

Methyl 2-(3-cyano-4-fluorophenyl)isonicotinate and sodium azide were dissolved in a DMF solution, followed by stirring at 50° C. for 4 hours to obtain methyl 2-(4-azido-3-cyanophenyl)isonicotinate. NMRC: 7.38 (1H, d), 7.84 (1H, dd), 8.46 (1H, d).

Reference Example 13

5-Formyl-2-methoxybenzonitrile, sodium acetate and hydroxyamine were dissolved in ethanol, followed by stirring at 80° C. for 6 hours to obtain 5-[(hydroxyimino)methyl]-2-methoxybenzonitrile. APN: 175.

Reference Example 14

5-[(Hydroxyimino)methyl]-2-methoxybenzonitrile, 4 M hydrochloric acid and Oxon (registered trade name) were dissolved in a solution of DMF, followed by stirring at room temperature for 12 hours to obtain 3-cyano-N-hydroxy-4-methoxybenzenecaboximidoyl chloride. NMRC: 7.01 (1H, d), 8.03 (1H, dd), 8.07 (1H, d).

Reference Example 15

3-Cyano-N-hydroxy-4-methoxybenzenecaboximidoyl chloride, ethyl propiolate and triethylamine were dissolved in a solution of THF, followed by stirring at 40° C. to obtain ethyl 3-(3-cyano-4-methoxyphenyl)-5-isoxazolecarboxylate. AP: 295.

Reference Example 16

Ethyl 3-(3-cyano-4-methoxyphenyl)-5-isoxazolecarboxylate and tribromoborane were dissolved in a solution of dichloromethane, followed by stirring for 2 hours under ice-cooling. Further, the mixture was stirred at 40° C. for 30 minutes to obtain ethyl 3-(3-cyano-4-hydroxyphenyl)-5-isoxazolecarboxylate. APN: 257.

Reference Example 17

Palladium-carbon was added to a methanol solution of methyl 2-(4-azido-3-cyanophenyl)isonicotinate, and the mixture was stirred in the presence of hydrogen gas at room temperature for 5 hours to obtain methyl 2-(4-amino-3-cyanophenyl)isonicotinate. AP: 254.

Reference Example 18

20% sodium ethoxide and isoamyl nitrite were added to and dissolved in an ethanol solution of 5-(cyanomethyl)-2-methoxybenzonitrile. Isopropyl alcohol was added, and the precipitate formed was collected by filtration. The resulting solid and 4-methylbenzenesulfonyl chloride were dissolved in ethanol, and the solution was refluxed for 5 hours to obtain 5-[cyano({[(4-methylphenyl)sulfonyl]oxy}imino)methyl]-2-methoxybenzonitrile. AP: 378.

Reference Example 19

Ethyl sulfanylacetate and triethylamine were dissolved in an ethanol solution of 5-[cyano({[(4-methylphenyl)sulfonyl]oxy}imino)methyl]-2-methoxybenzonitrile, followed by stirring for 5 hours under ice-cooling to obtain ethyl 4-amino-3-(3-cyano-4-methoxyphenyl)isothiazole-5-carboxylate. AP: 378.

Reference Example 20

3-Methylbutyl nitrate was dissolved in a tetrahydrofuran solution of ethyl 4-amino-3-(3-cyano-4-methoxyphenyl)isothiazole-5-carboxylate, followed by heating under reflux for 5 hours to obtain ethyl 3-(3-cyano-4-methoxyphenyl)isothiazole-5-carboxylate. AP: 311.

Reference Example 21

Under ice-cooling, boron tribromide was added to a dichloromethane solution of ethyl 3-(3-cyano-4-methoxyphenyl)isothiazole-5-carboxylate, followed by stirring for 1 hour and then stirring at 40° C. for 3 hours to obtain ethyl 3-(3-cyano-4-hydroxyphenyl)isothiazole-5-carboxylate. AP: 297.

Reference Examples 22 to 35

Starting from the corresponding starting compounds, a compound of Reference Example 22 was produced in the same manner as in Reference Example 2, a compound of Reference Example 23 was produced in the same manner as in Reference Example 3, a compound of Reference Example 24 was produced in the same manner as in Reference Example 4, a compound of Reference Example 25 was produced in the same manner as in Reference Example 6, compounds of Reference Examples 26 to 27 were produced in the same manner as in Reference Example 8, and compounds of Reference Examples 28 to 35 were produced in the same manner as in Reference Example 9. As the starting compound in Reference Examples 32 and 34, used was the phenol compound described in Patent References 7 and 8. The structures and the physicochemical data of the compounds of Reference Examples 22 to 35 are shown in Table 1 below.

Example 1

(1) 87 mg of tetrakis(triphenylphosphine)palladium was added to a toluene (25 ml) suspension of 966 mg of methyl 2-(3-cyano-4-{[(trifluoromethyl)sulfonyl]oxy}phenyl)isonicotinate, 610 mg of phenylboronic acid and 518 mg of potassium carbonate, followed by heating at 100° C. in an argon atmosphere for 2 hours. Water was added to the reaction mixture, followed by extraction with ethyl acetate. The organic layer was washed with brine, dried and concentrated under reduced pressure. The residue was purified by silica gel column chromatography (hexane:ethyl acetate=95:5 to 70:30) to obtain 758 mg of methyl 2-(2-cyanobiphenyl-4-yl)isonicotinate.

(2) 758 mg of this compound was dissolved in a mixture of 10 ml of methanol and 10 ml of THF, and 7.2 ml of aqueous 1 M sodium hydroxide solution was added thereto, followed by heating at 60° C. for 13 hours. The reaction mixture was cooled to room temperature, neutralized with 1 M hydrochloric acid, and concentrated under reduced pressure. The residue was recrystallized from a mixture of ethanol and water to obtain 472 mg of 2-(2-cyanobiphenyl-4-yl)isonicotinic acid.

(3) 414 mg of this compound was dissolved in 15 ml of ethanol, and 1.5 ml of aqueous 1 M sodium hydroxide solution was added thereto, followed by stirring at room temperature for 30 minutes. The reaction solution was concentrated under reduced pressure to obtain 430 mg of sodium 2-(2-cyanobiphenyl-4-yl)isonicotinate.

Example 2

(1) 212 mg of methyl 2-(3-cyano-4-fluorophenyl)isonicotinate and 68 mg of pyrazole were dissolved in 4 ml of DMSO, and 102 mg of potassium tert-butoxide was added, followed by stirring at room temperature for 30 minutes. The reaction mixture was diluted with water, and extracted with ethyl acetate. The organic layer was washed with brine, dried and concentrated under reduced pressure. The resulting residue was purified by silica gel column chromatography (hexane:ethyl acetate=67:33) to obtain 251 mg of methyl 2-[3-cyano-4-(1H-pyrazol-1-yl)phenyl]isonicotinate.

(2) 236 mg of this compound was dissolved in a mixture liquid of 10 ml of methanol and 5 ml of THF, and 1.16 ml of aqueous 1 M sodium hydroxide solution was added, followed by heating at 80° C. for 40 minutes. The reaction liquid was cooled to room temperature, washed with water, and the organic solvent was evaporated away under reduced pressure. The reaction liquid was washed with diethyl ether to obtain an aqueous layer. The aqueous layer was neutralized with 1 M hydrochloric acid, followed by extraction with ethyl acetate. The organic layer was washed with brine, dried and concentrated under reduced pressure, and the resulting residue was recrystallized from a mixture of ethanol and water to obtain 103 mg of 2-[3-cyano-4-(1H-pyrazol-1-yl)phenyl]isonicotinic acid.

(3) 92 mg of this compound was dissolved in ethanol, and 0.317 ml of aqueous 1 M sodium hydroxide solution was added thereto, followed by stirring at room temperature for 15 minutes. The reaction liquid was concentrated, the residue was suspended in 2-propanol, and the precipitate was collected by filtration to obtain 93 mg of sodium 2-[3-cyano-4-(1H-pyrazol-1-yl)phenyl]isonicotinate.

Example 3

(1) 1.32 g of methyl 2-[4'-(benzyloxy)-2,3'-dicyanobiphenyl-4-yl]isonicotinate, which had been obtained in the same manner as in Example 1(1) using 4-(benzyloxy)-3-cyanophenyl]boric acid and methyl 2-(3-cyano-4-{[(trifluoromethyl)sulfonyl]oxy}phenyl)isonicotinate, was dissolved in a mixture of 50 ml of THF and 50 ml of methanol, and 0.5 g of palladium-carbon was added, followed by stirring in a hydrogen atmosphere at room temperature for 12 hours. The reaction mixture was filtered, and the filtrate was concentrated under reduced pressure to obtain 0.5 g of methyl 2-(2,3'-dicyano-4'-hydroxybiphenyl-4-yl)isonicotinate.

(2) 230 mg of this compound was dissolved in DMF, and 50 μL of iodomethane and 108 mg of potassium carbonate were added, followed by stirring at room temperature for 2 hours. Water was added to the reaction mixture, followed by extraction with ethyl acetate. The organic layer was washed with brine, dried and concentrated under reduced pressure. Chloroform was added to the residue, and the precipitated crystal was collected by filtration, followed by washing with chloroform to obtain 73 mg of methyl 2-(2,3'-dicyano-4'-methoxybiphenyl-4-yl)isonicotinate.

(3) 73 mg of this compound was dissolved in 2 ml of methanol and 2 ml of THF, and 220 μL of an aqueous 1 M sodium hydroxide solution was added, followed by heating at 60° C. for 2 hours. After cooling, the solvent was removed under reduced pressure, and then water was added to the residue, followed by neutralization with 1 M hydrochloric acid. The precipitated crystal was collected by filtration and washed with a mixture of ethanol and water to obtain 64 mg of 2-(2,3'-dicyano-4'-methoxybiphenyl-4-yl)isonicotinic acid.

Example 4

58 mg of tetrakis(triphenylphosphine)palladium and 208 mg of potassium carbonate were added to a toluene (10 ml) solution of 386 mg of methyl 2-(3-cyano-4-{[(trifluoromethyl)sulfonyl]oxy}phenyl)isonicotinate and 534 mg of 1-(triisopropylsilyl)pyrrole-3-boronic acid, then this was irradiated with microwaves and heated at 130° C. in a nitrogen atmosphere for 1 hour. Water was added to the reaction mixture, followed by extraction with ethyl acetate. The organic layer was washed with brine, dried and concentrated under reduced pressure. The residue was purified by silica gel column chromatography (hexane:ethyl acetate=95:5 to 70:30) to obtain 24 mg of methyl 2-{3-cyano-4-[1-(triisopropylsilyl)-1H-pyrrol-3-yl]phenyl}isonicotinate.

(2) 24 mg of this compound was dissolved in 1 ml of THF, and 63 μL of 1 M tetrabutylammonium fluoride/THF solution was added thereto, followed by stirring at room temperature for 15 hours. The reaction mixture was concentrated under reduced pressure, and the residue was purified by silica gel column chromatography (hexane:ethyl acetate=90:10 to 70:30) to obtain 6 mg of methyl 2-[3-cyano-4-(1H-pyrrol-3-yl)phenyl]isonicotinate.

(3) 6 mg of this compound was dissolved in a mixture of 0.5 ml of methanol and 0.5 ml of THF, and 22 μl of aqueous 1 M sodium hydroxide solution was added, followed by heating at 60° C. for 2 hours. The reaction liquid was cooled, and the solvent was removed under reduced pressure. Water was added to the residue, followed by neutralization with 1 M hydrochloric acid. The precipitated crystal was collected by filtration and washed with a mixture of ethanol and water to obtain 1.5 mg of 2-[3-cyano-4-(1H-pyrrol-3-yl)phenyl]isonicotinic acid.

Example 5

(1) 131 mg of methyl 2-(4-amino-3-cyanophenyl)isonicotinate and 67 μl of 2,5-dimethoxytetrahydrofuran were dissolved in 1.3 ml of acetic acid solution, followed by heating and stirring at 100° C. for 4 hours. The solution was poured into water, followed by extraction with ethyl acetate. The solvent of the organic layer was evaporated under reduced pressure, and the residue was purified by column chromatography (hexane:ethyl acetate=10:1 to 1:1) to obtain 100 mg of methyl 2-[3-cyano-4-(1H-pyrrol-1-yl)phenyl]isonicotinate.

(2) 100 mg of methyl 2-[3-cyano-4-(1H-pyrrol-1-yl)phenyl]isonicotinate was dissolved in a mixture of 2 ml of methanol and 3 ml of THF, and 66 μl of aqueous 1 M sodium hydroxide solution was added, followed by heating under reflux for 3 hours. The reaction mixture was cooled, then neutralized with 66 μl of 1 M hydrochloric acid, followed by extraction with a mixture of 2-propanol and chloroform (1:4). The organic layer was washed with brine. The solvent of the organic layer was evaporated under reduced pressure, and the resulting residue was recrystallized from a mixture of 2-propanol and chloroform (1:4) to obtain 95 mg of 2-[3-cyano-4-(1H-pyrrol-1-yl)phenyl]isonicotinic acid.

Example 6

(1) 200 mg of methyl 2-(4-azido-3-cyanophenyl)isonicotinate, 54 μl of ethynylbenzene, 72 μl of aqueous 1 M sodium L(+)-ascorbate solution and 2 mg of copper sulfate were added to a mixture of 1.4 ml of water and 1.4 ml of 2-propanol, followed by vigorous stirring overnight at room temperature. The reaction mixture was diluted with 5 ml of water, the precipitate formed was collected by filtration, washed with iced cool water, and dried under reduced pressure to obtain 12 mg of methyl 2-[3-cyano-4-(4-phenyl-1H-1,2,3-triazol-1-yl)phenyl]isonicotinate.

(2) 12 mg of methyl 2-[3-cyano-4-(4-phenyl-1H-1,2,3-triazol-1-yl)phenyl]isonicotinate was dissolved in a mixture of 234 μl of methanol and 351 μl of THF, then 61 μl of aqueous 1 M sodium hydroxide solution was added, followed by heating under reflux for 3 hours. The reaction mixture was cooled, and neutralized with 61 μl of 1 M hydrochloric acid, then extracted with a mixture of 2-propanol and chloroform (1:4). The organic layer was washed with brine. The solvent of the organic layer was removed under reduced pressure, and the resulting residue was recrystallized from a mixture of 2-propanol and chloroform (1:4) to obtain 4 mg of 2-[3-cyano-4-(4-phenyl-1H-1,2,3-triazol-1-yl)phenyl]isonicotinic acid.

Example 7

(1) A toluene (0.5 ml) suspension of 20 mg of methyl 5-(3-cyano-4-{[(trifluoromethyl)sulfonyl]oxy}phenyl)thiophene-2-carboxylate and 10 mg of potassium carbonate was added to 15 mg of 3-aminobenzeneboronic acid monohydrate, and in an argon atmosphere, 8 mg of tetrakis(triphenylphosphine)palladium was added thereto. The mixture was stirred overnight at 100° C., then cooled to room temperature, and filtered through Celite. The solvent was evaporated under reduced pressure to obtain methyl 5-(3'-amino-2-cyanobiphenyl-4-yl)thiophene-2-carboxylate.

(2) 0.2 ml of aqueous 1 M sodium hydroxide solution was added to a methanol (0.25 ml)/tetrahydrofuran (0.25 ml) solution of methyl 5-(3'-amino-2-cyanobiphenyl-4-yl)thiophene-2-carboxylate, followed by stirring overnight at 60° C. 1 M hydrochloric acid was added to the reaction liquid to make it acidic, and the solvent was evaporated under reduced pressure. The residue was purified by HPLC [elution through column: SunFire (registered trademark) C18 5 μm, 19 mm×100 mm, solvent: MeOH/aqueous 0.1% formic acid solution 10/90 for 1 minute, ratio change to 95/5, taking 8 minutes, and further elution with 95/5 for 3 minutes, flow rate: 25 mL/min), thereby obtaining 2.5 mg of 5-(3'-amino-2-cyanobiphenyl-4-yl)thiophene-2-carboxylic acid.

Example 8

In the same manner as in Example 7 but using 25 mg of {4-[(tert-butoxycarbonyl)amino]-3-fluorophenyl}boronic acid in place of 3-aminobenzeneboronic acid monohydrate, 5-{4'-[(tert-butoxycarbonyl)amino]-2-cyano-3'-fluorobiphenyl-4-yl}thiophene-2-carboxylic acid was obtained. The compound was dissolved in a mixed solvent of 0.5 ml of dichloromethane and 0.5 ml of trifluoroacetic acid, followed by stirring at room temperature for 2 hours. The reaction liquid was evaporated under reduced pressure, and then purified in the same manner as that for the purification treatment in Example 7 to obtain 9.2 mg of 5-(4'-amino-2-cyano-3'-fluorobiphenyl-4-yl)thiophene-2-carboxylic acid.

Example 9

(1) 6 ml of aqueous 2 M sodium carbonate solution and 70 mg of tetrakistriphenylphosphine palladium were added to a toluene (15 ml) solution of 450 mg of (3-cyano-4-pyridin-3-ylphenyl)boronic acid and 412 mg of 2-chloroisonicotinic acid, and in an argon atmosphere, this was heated at 100° C. for 2 hours. 3 ml of ethanol was added, followed by further heating at 100° C. for 1 hour. Water was added to the reaction mixture, followed by extraction with chloroform. The organic layer was washed with brine, dried and concentrated under reduced pressure. The residue was purified by silica gel column chromatography (chloroform:methanol=99:1 to 93:7) to obtain 127 mg of ethyl 2-(3-cyano-4-pyridin-3-ylphenyl)isonicotinate. F: 330.

(2) 100 mg of this compound was dissolved in a mixture of 10 ml of methanol and 3 ml THF, and 30 ml of aqueous 1 M sodium hydroxide solution was added thereto and heated at 60° C. for 1.5 hours. After cooled to room temperature, the reaction mixture was made to have pH of 3 to 4 with 1 M hydrochloric acid added thereto, and then concentrated under reduced pressure. The residue was washed with a mixture of ethanol and water to obtain 54 mg of 2-(3-cyano-4-pyridin-3-ylphenyl)isonicotinic acid 0.3 hydrochloride.

Examples 10 to 153

In the same manner as in Examples 1 to 8 but starting from the corresponding starting compounds, the compounds of Examples 10 to 153 shown in Tables 2 to 11 below were produced. The structures and the physicochemical data of the compounds of Examples 1 to 153 are shown in Tables 2 to 11.

Structures of other compounds of the present invention are shown in Tables 12 and 13. These can be readily produced according to the above-mentioned production methods, or according to the methods described in Examples, or according to methods self-obvious to those skilled in the art, or according their modifications.

TABLE 1
| REx | Str | Dat |
|---|---|---|
| 22 | 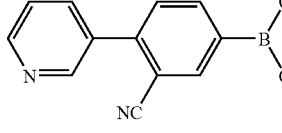 | F: 281 (G-2W) |
| 23 | 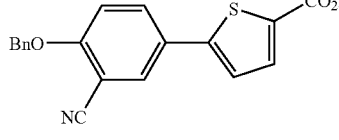 | F: 350 |
| 24 | 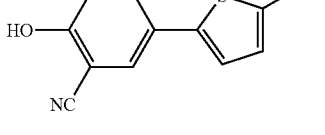 | FN: 258 |
| 25 | 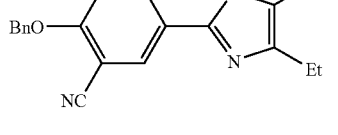 | AP: 401 (Na) |
| 26 | 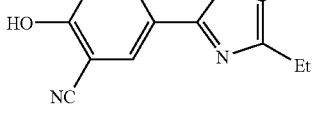 | APN: 287 |
| 27 | 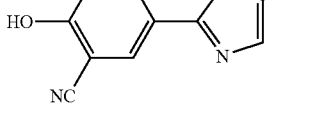 | APN: 259 |
| 28 | 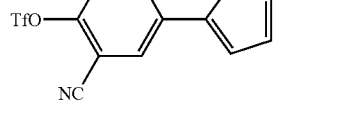 | F: 392 |
| 29 | 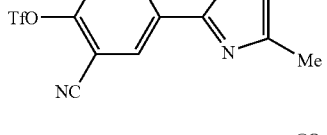 | F: 421 |
| 30 | 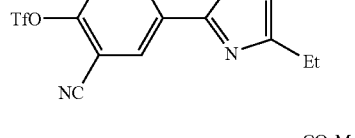 | AP: 443 (Na) |
| 31 | 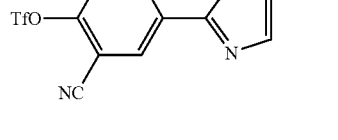 | AP: 415 (Na) |
TABLE 1-continued
| REx | Str | Dat |
|---|---|---|
| 32 | 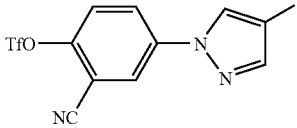 | AP: 412 (Na) |
| 33 | 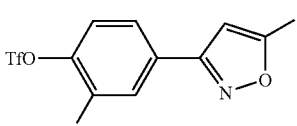 | AP: 413 (Na) |
| 34 | 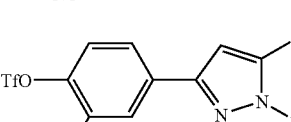 | AP: 412 (Na) |
| 35 | 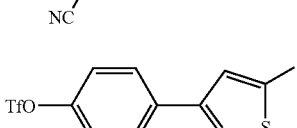 | AP: 429 (Na) |
TABLE 2
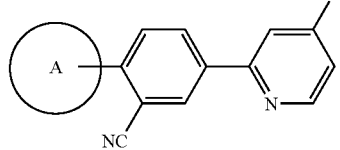
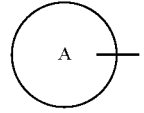
| Ex | Syn | | Sal | Dat |
|---|---|---|---|---|
| 1 | 1 | Ph- | Na | F: 301; NMR: 8.33 (1H, s), 8.55 (1H, dd), 8.64 (1H, d) |
| 2 | 2 | 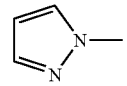 | Na | FN: 289; NMR: 6.67 (1H, t), 7.95 (1H, d), 8.66 (1H, d) |
| 3 | 3 | 4-MeO-3-CN-Ph- | | APN: 354; NMR: 4.01 (3H, s), 8.47 (1H, s), 8.87 (1H, d) |
| 4 | 4 | 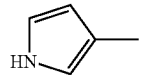 | | APN: 288; NMR: 7.84 (1H, d), 8.49 (1H, d), 8.79 (1H, d) |
| 5 | 5 | 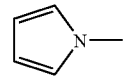 | | APN: 288; NMR: 6.39 (2H, t), 7.76 (1H, d), 8.50 (1H, s) |
| 6 | 6 | Ph- 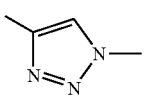 | | APN: 366; NMR: 8.59 (1H, s), 8.76 (1H, dd), 9.34 (1H, s) |

TABLE 2-continued

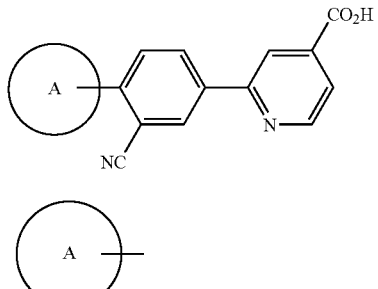

| Ex | Syn | A | Sal | Dat |
|---|---|---|---|---|
| 9 | 9 | 3Py- | 0.3HCl | ES: 302; NMR: 8.52 (1H, s), 8.60 (1H, dd), 8.93 (1H, d) |
| 10 | 1 | 4-F-Ph- | | FN: 317; NMR: 8.50 (1H, s), 8.46 (1H, dd), 8.92 (1H, d) |
| 11 | 1 | 3-MeO-Ph- | | FN: 329; NMR: 3.85 (3H, s), 7.86 (1H, dd), 8.54 (1H, dd) |
| 12 | 1 | 4-MeO-Ph- | Na | F: 331; NMR: 3.85 (3H, s), 7.12 (2H, d), 8.42 (1H, dd) |
| 13 | 1 | 4-Cl-Ph- | | FN: 333; NMR: 8.50 (1H, s), 8.56 (1H, dd), 8.92 (1H, d) |
| 14 | 1 | 4-CF$_3$-Ph- | Na | FN: 367; NMR: 8.37 (1H, s), 8.51 (1H, dd), 8.67 (1H, d) |
| 15 | 1 | 2-MeO-Ph- | | F: 331; NMR: 3.80 (3H, s), 7.65 (1H, d), 8.91 (1H, dd) |
| 16 | 1 | 4-Me-Ph- | Na | F: 315; NMR: 2.40 (3H, s), 7.37 (2H, d), 8.44 (1H, dd) |
| 17 | 1 | 2Thie- | | F: 307; NMR: 7.29 (1H, dd), 8.49 (1H, s), 8.51 (1H, dd) |

TABLE 3

| Ex | Syn | A | Sal | Dat |
|---|---|---|---|---|
| 18 | 1 | 3Thie- | Na | ES: 307; NMR: 7.57 (1H, dd), 8.34 (1H, s), 8.43 (1H, dd) |
| 19 | 1 | 3Fur- | | F: 291; NMR: 7.10 (1H, dd), 8.50 (1H, dd), 8.66 (1H, d) |
| 20 | 1 | 4-NC-Ph- | | FN: 324; NMR: 8.52 (1H, s), 8.59 (1H, dd), 8.92 (1H, d) |
| 21 | 1 | 4-HOOC-Ph- | | F: 345; NMR: 8.11 (2H, d), 8.59 (1H, dd), 8.92 (1H, d) |
| 22 | 1 | 2Fur- | | FN: 289; NMR: 6.78 (1H, dd), 7.37 (1H, d), 8.57 (1H, dd) |
| 23 | 1 | 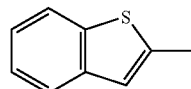 | 0.3HCl | FN: 289; NMR: 7.83 (1H, dd), 7.92 (1H, d), 8.89 (1H, d) |
| 24 | 1 | 4-iBuO-Ph- | | FN: 371; NMR: 1.01 (6H, s), 7.12 (2H, d), 8.51 (1H, dd) |
| 25 | 1 | 4-Et-Ph- | | FN: 327; NMR: 1.25 (3H, t), 7.41 (2H, d), 8.53 (1H, dd) |
| 26 | 1 | 3-Me-Ph- | | FN: 313; NMR: 2.42 (3H, s), 7.86 (1H, dd), 8.54 (1H, dd) |
| 27 | 1 | 2-Me-Ph- | | FN: 313; NMR: 2.19 (3H, s), 7.87 (1H, dd), 8.53 (1H, dd) |
| 28 | 1 | 3-Cl-Ph- | | Anal: Calc. C; 68.17%, H; 3.31%, N; 8.37%, Cl; 10.59% Found C; 67.90%, H; 3.51%, N; 8.23%, Cl; 10.43%; NMR: 8.51 (1H, s), 8.56 (1H, d), 8.92 (1H, d) |

TABLE 3-continued

| Ex | Syn | A | Sal | Dat |
|---|---|---|---|---|
| 29 | 1 | 2-Cl-Ph- | Na | FN: 333; NMR: 7.74 (1H, dd), 8.44 (1H, dd), 8.68 (1H, d) |
| 30 | 1 | 4-tBu-Ph- | Na | FN: 355; NMR: 1.35 (9H, s), 7.86 (1H, dd), 8.69 (1H, d) |
| 31 | 1 | 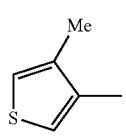 | | FN: 319; NMR: 2.17 (3H, s), 7.86 (1H, d), 8.92 (1H, d) |
| 32 | 1 | 4-HO-Ph- | | FN: 315; NMR: 6.94 (2H, d), 8.49 (1H, dd), 8.90 (1H, d) |
| 33 | 1 | 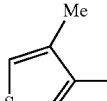 | Na | FN: 319; NMR: 2.54 (3H, s), 7.54 (1H, d), 8.64 (1H, d) |
| 34 | 1 | 3,5-di(CF$_3$)-Ph- | | APN: 435; NMR: 8.30 (1H, s), 8.61 (1H, dd), 8.93 (1H, d) |

TABLE 4

| Ex | Syn | A | Sal | Dat |
|---|---|---|---|---|
| 35 | 1 | 2Naph- | | APN: 349; NMR: 7.59-7.69 (2H, m), 8.61 (1H, dd), 8.93 (1H, d) |
| 36 | 1 | 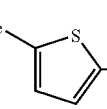 | | APN: 367; NMR: 8.03 (1H, s), 8.58 (1H, dd), 8.92 (1H, d) |
| 37 | 1 | 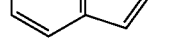 | | APN: 375; NMR: 7.37-7.59 (2H, m), 8.57 (1H, dd), 8.92 (1H, d) |
| 38 | 1 | 4-BnO-3-NC-Ph- | | APN: 430; NMR: 5.40 (2H, s), 7.99 (1H, dd), 8.91 (1H, d) |
| 39 | 1 | 2,4-diMeO-Ph- | | APN: 359; NMR: 3.85 (3H, s), 7.85 (1H, dd), 8.90 (1H, d) |
| 40 | 1 | 4-MeS-Ph- | | APN: 345; NMR: 2.56 (3H, s), 8.53 (1H, dd), 8.91 (1H, d) |
| 41 | 1 | 4-(CF$_3$)O-Ph- | | APN: 383; NMR: 7.58 (2H, d), 8.57 (1H, dd), 8.92 (1H, d) |
| 42 | 1 | 4-EtO-Ph- | | APN: 343; NMR: 4.12 (2H, q), 7.85 (1H, dd), 8.90 (1H, d) |
| 43 | 1 | 4-PhO-Ph- | | APN: 391; NMR: 7.12-7.18 (4H, m), 7.86 (1H, dd), 8.53 (1H, dd) |
| 44 | 1 | 3,4-diMeO-Ph- | | APN: 359; NMR: 3.85 (6H, d), 7.85 (1H, dd), 8.90 (1H, d) |
| 45 | 1 | 4-Me$_2$N-Ph- | | APN: 342; NMR: 3.00 (6H, s), 7.83 (1H, dd), 8.89 (1H, d) |
| 46 | 1 | 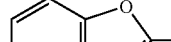 | | APN: 343; NMR: 6.14 (2H, s), 7.85 (1H, dd), 8.91 (1H, d) |
| 47 | 1 | 3-Ph-Ph- | | APN: 375; NMR: 7.35-7.60 (3H, m), 8.57 (1H, dd), 8.91 (1H, d) |
| 48 | 1 | 4-MeO-3-Me-Ph- | | APN: 343; NMR: 2.24 (3H, s), 7.85 (1H, dd), 8.90 (1H, d) |
| 49 | 1 | 4-MeO-3,5-diMe-Ph- | | APN: 357; NMR: 3.74 (3H, s), 7.85 (1H, dd), 8.90 (1H, d) |
| 50 | 1 | 3-Me-4-(CF$_3$)O-Ph- | | APN: 397; NMR: 2.39 (3H, s), |

TABLE 4-continued

| | | | |
|---|---|---|---|
| 51 | 1 | 2-Ph-Ph- | 8.56 (1H, dd), 8.92 (1H, d) APN: 375; NMR: 8.36 (1H, dd), 8.53 (1H, d), 8.87 (1H, d) |

TABLE 5

| | | | |
|---|---|---|---|
| 52 | 1 | 4Py- | APN: 300; NMR: 8.51 (1H, s), 8.60 (1H, dd), 8.91 (1H, d) |
| 53 | 1 | 4-MeO-2,5-diMe-Ph- | APN: 357; NMR: 2.16 (6H, s), 7.86 (1H, dd), 8.91 (1H, d) |
| 54 | 1 | 4-nBuO-Ph- | APN: 371; NMR: 0.96 (3H, t), 7.85 (1H, dd), 8.90 (1H, d) |
| 55 | 1 | 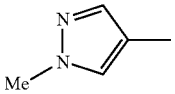 | APN: 303; NMR: 3.95 (3H, s), 8.06 (1H, s), 8.87 (1H, d) |
| 56 | 1 | 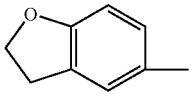 | APN: 341; NMR: 4.63 (2H, t), 7.72 (1H, d), 8.90 (1H, dd) |
| 57 | 2 | 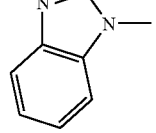 | Na F: 363 (Na); NMR: 7.25-7.43 (2H, m), 7.94 (1H, d), 8.68 (1H, s) |
| 58 | 2 | 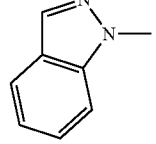 | Na F: 341; NMR: 7.35 (1H, t), 8.41 (1H, s), 8.69 (1H, d) |
| 59 | 2 | 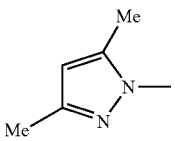 | Na F: 319; NMR: 2.22 (3H, s), 8.38 (1H, s), 8.67 (1H, d) |

TABLE 5-continued

| | | | |
|---|---|---|---|
| 60 | 2 |  | APN: 303; NMR: 7.74 (1H, s), 8.71 (1H, d), 8.88 (1H, d) |
| 61 | 2 |  | AP: 328; NMR: 7.26 (1H, s), 7.98 (1H, s), 8.60 (1H, d) |
| 62 | 2 |  | APN: 290; NMR: 7.89 (1H, dd), 8.42 (1H, s), 9.29 (1H, s) |
| 63 | 2 | 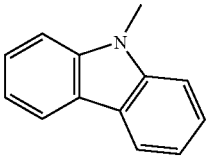 | APN: 388; NMR: 8.28 (1H, s), 8.32 (1H, s), 8.59 (1H, s) |
| 64 | 2 | 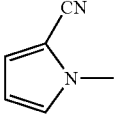 | APN: 313; NMR: 7.69 (1H, dd), 8.56 (1H, s), 8.69 (1H, dd) |
| 65 | 6 | 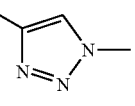 | APN: 334; NMR: 4.61 (2H, s), 8.03 (1H, d), 8.57 (1H, s) |
| 66 | 1 | 3-CF$_3$-Ph- | APN: 367; NMR: 8.03 (1H, s), 8.58 (1H, dd), 8.92 (1H, d) |
| 67 | 1 | 4-Ph-Ph- | APN: 375; NMR: 7.37-7.59 (2H, m), 8.57 (1H, dd), 8.92 (1H, d) |

TABLE 6

| Ex | Syn | | Sal Dat |
|---|---|---|---|
| 7 | 7 | 3-H$_2$N-Ph- | ES: 321; H: 1.93 |
| 8 | 8 | 4-H$_2$N-3-F-Ph- | ES: 339; H: 2.51 |
| 68 | 1 | Ph- | Na FN: 304; NMR: 7.23 (1H, d), 7.99 (1H, dd), 8.21 (1H, d) |
| 69 | 1 | 4-Me-Ph- | Na FN: 318; NMR: 2.39 (3H, s), 7.24 (1H, d), 7.35 (2H, d) |
| 70 | 1 | 4-MeO-Ph- | Na FN: 334; NMR: 3.84 (3H, s), 7.22 (1H, d), 7.95 (1H, dd) |
| 71 | 1 | 4-CF$_3$-Ph- | Na F: 374; NMR: 7.25 (1H, d), 8.03 (1H, dd), 8.27 (1H, d) |

TABLE 6-continued

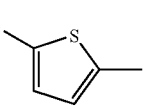

| Ex | Syn | | Sal | Dat |
|---|---|---|---|---|
| 72 | 1 | 4-Cl-Ph- | Na | FN: 338; NMR: 7.20 (1H, d), 7.58-7.68 (5H, m), 8.22 (1H, d) |
| 73 | 7 | 3Py- | | ES: 307 |
| 74 | 7 | 3-Me-Ph- | | ES: 320 |
| 75 | 7 | 2-Me-Ph- | | ES: 320; H: 2.94 |
| 76 | 7 | 3-HO-Ph- | | ES: 322; H: 2.50 |
| 77 | 7 | 2,3-diMe-Ph- | | ES: 334 |
| 78 | 7 | 3-MeO-Ph- | | ES: 336; H: 2.91 |
| 79 | 7 | 2-MeO-Ph- | | ES: 336 |
| 80 | 7 | MeO-(2-methoxy-5-pyridyl) | | ES: 337 |
| 81 | 7 | 2-Cl-Ph- | | ES: 340; H: 2.90 |
| 82 | 7 | 5-indolyl (1H-indol-5-yl) | | ES: 345; H: 2.80 |
| 83 | 7 | 4-Ac-Ph- | | ES: 348; H: 2.68 |
| 84 | 7 | 4-Me$_2$N-Ph- | | ES: 349; H: 2.92 |
| 85 | 7 | 3-Me$_2$N-Ph- | | ES: 349; H: 2.49 |
| 86 | 7 | 3-HOOC-Ph- | | ES: 350 |
| 87 | 7 | 5-Ac-thien-2-yl | | ES: 354 |

TABLE 7

| 88 | 7 | 1Naph- | ES: 356 |
| 89 | 7 | 2Naph- | ES: 356; H: 3.38 |
| 90 | 7 | 8-quinolyl | ES: 357 |
| 91 | 7 | 1-Me-indol-5-yl | ES: 359; H: 3.15 |
| 92 | 7 | benzothien-2-yl | ES: 362; H: 3.67 |
| 93 | 7 | benzothien-3-yl | ES: 362; H: 3.15 |
| 94 | 7 | 4-tBu-Ph- | ES: 362; H: 3.54 |
| 95 | 7 | 3-AcNH-Ph- | ES: 363; H: 2.44 |
| 96 | 7 | 3-HOOC-Ph- | ES: 350 |
| 97 | 7 | 3,4-diMeO-Ph- | ES: 366 |
| 98 | 7 | 2,4-diMeO-5-pyrimidinyl | ES: 368 |
| 99 | 7 | 2-CF$_3$-Ph- | ES: 374; H: 2.92 |
| 100 | 7 | 4-(pyrrolidin-1-yl)-Ph- | ES: 375 |
| 101 | 7 | 3-[Me$_2$N(CO)]-Ph- | ES: 377 |

TABLE 7-continued

| | | | |
|---|---|---|---|
| 102 | 7 | 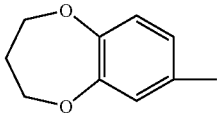 | ES: 378; H: 2.96 |
| 103 | 7 | 3-Ph-Ph- | ES: 382; H: 3.46 |
| 104 | 7 | 3-[MeS(O)₂]-Ph- | ES: 384 |
| 105 | 7 | 4-cHex-Ph- | ES: 388; H: 3.84 |
| 106 | 7 | 2-(CF₃)O-Ph- | ES: 390 |
| 107 | 7 | 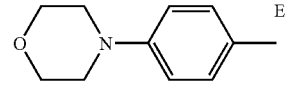 | ES: 391; H: 2.96 |
| 108 | 7 | 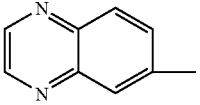 | ES: 358 |

TABLE 8

| | | | |
|---|---|---|---|
| 109 | 7 | 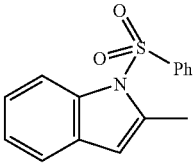 | ES: 396; H: 3.37 |
| 110 | 7 | 4-PhO-Ph- | ES: 398; H: 3.46 |
| 111 | 7 | 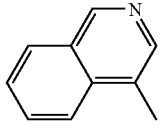 | ES: 412; H: 3.46 |
| 112 | 7 | 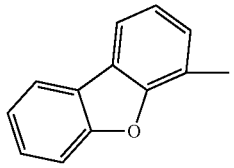 | ES: 389 |
| 113 | 8 | 4-H₂N-3-MeO-Ph- | ES: 351; H: 3.19 |
| 114 | 7 | 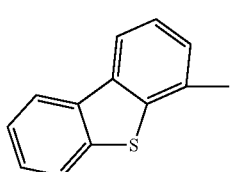 | ES: 554; H: 3.02 |
| 115 | 7 | 4-AcNH-Ph- | ES: 363; H: 2.43 |
| 116 | 7 | 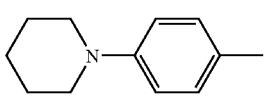 | ES: 386; H: 3.43 |
| 117 | 7 | 2-PhO-Ph- | ES: 398 |
| 118 | 7 | 4-[Ph(CO)]-Ph- | ES: 410; H: 3.20 |

TABLE 8-continued

| | | | |
|---|---|---|---|
| 119 | 7 | 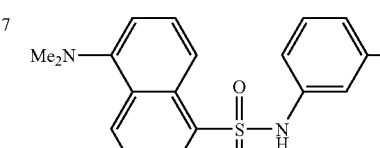 | ES: 485 |
| 120 | 7 | 4-iPrO-Ph- | ES: 364; H: 3.26 |
| 121 | 7 | 4-BnO-Ph- | ES: 412; H: 3.51 |
| 122 | 7 | 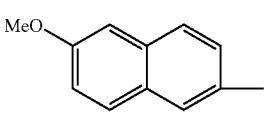 | ES: 357; H: 2.07 |

TABLE 9

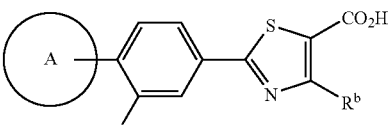

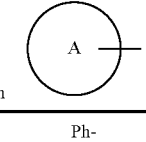

| Ex | Syn | A | $R^b$— | Sal | Dat |
|---|---|---|---|---|---|
| 123 | 1 | Ph- | Me- | | AP: 321; NMR: 2.71 (3H, s), 7.78 (1H, d), 8.49 (1H, d) |
| 124 | 1 | 4-Me-Ph- | Me- | Na | F: 335; NMR: 2.40 (3H, s), 7.37 (2H, d), 8.20 (1H, dd) |
| 125 | 1 | 4-Et-Ph- | Me- | | AP: 349; NMR: 2.65-2.76 (5H, m), 7.41 (2H, d), 8.47 (1H, d) |
| 126 | 1 | 4-(CF₃)O-Ph- | Me- | | AP: 405; NMRC: 2.70 (3H, s), 7.58 (2H, d), 8.51 (1H, d) |
| 127 | 1 | 4-MeO-Ph- | Me- | | AP: 351; NMR: 2.70 (3H, s), 3.85 (3H, s), 8.44 (1H, d) |
| 128 | 1 | 3-MeO-Ph- | Me- | | AP: 373 (Na); NMR: 2.71 (3H, s), 3.84 (3H, s), 8.48 (1H, d) |
| 129 | 1 | 3-Me-Ph- | Me- | | AP: 335; NMR: 2.41 (3H, s), 2.70 (3H, s), 8.32 (1H, dd) |
| 130 | 1 | 4-tBu-Ph- | Me- | | APN: 375; NMR: 1.35 (9H, s), 2.71 (3H, s), 7.77 (1H, d) |
| 131 | 1 | 3Fur- | Me- | | APN: 309; NMR: 2.70 (3H, s), 7.10 (1H, dd), 8.29 (1H, dd) |
| 132 | 1 | 3Thie- | Me- | | APN: 325; NMR: 2.70 (3H, s), 7.57 (1H, dd), 7.87 (1H, d) |
| 133 | 1 | 4-Me₂N-Ph- | Me- | | APN: 362; NMR: 2.70 (3H, s), 3.00 (6H, s), 7.71 (1H, d) |
| 134 | 1 | Ph- | Et- | | AP: 357 (Na); NMR: 3.14 (2H, q), 7.52-7.70 (5H, m), 7.78 (1H, d) |
| 135 | 1 | 4-Me-Ph- | Et- | | AP: 371 (Na); NMR: 1.29 (3H, t), 2.40 (3H, s), 7.75 (1H, |

TABLE 9-continued

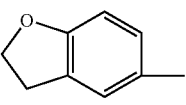

| Ex | Syn | R$^b$— | Sal | Dat |
|---|---|---|---|---|
| 136 | 1 | Ph- | H— | APN: 305; NMR: 7.52-7.61 (3H, m), 7.81 (1H, d), 8.50 (1H, s) |

TABLE 10

| Ex | Syn | A | Dat |
|---|---|---|---|
| 137 | 1 | Ph- | APN: 288; NMR: 7.46-7.69 (5H, m), 8.55 (1H, d), 9.23 (1H, s) |
| 138 | 1 | 4-Me-Ph- | APN: 302; NMR: 2.40 (3H, s), 8.52 (1H, d), 9.22 (1H, s) |
| 139 | 1 | 2Thie- | APN: 294; NMR: 7.28 (1H, dd), 7.90 (1H, d), 8.16 (1H, s) |
| 140 | 1 | 4-MeO-Ph- | APN: 318; NMR: 3.84 (3H, s), 7.75 (1H, d), 8.51 (1H, d) |
| 141 | 1 | 3-Me-Ph- | APN: 302; NMR: 2.41 (3H, s), 7.77 (1H, d), 8.17 (1H, s) |
| 142 | 1 | 4-tBu-Ph- | APN: 344; NMR: 1.35 (9H, s), 7.58 (4H, s), 8.16 (1H, s) |
| 143 | 1 | 3Fur- | APN: 278; NMR: 7.08 (1H, dd), 7.90 (1H, d), 9.21 (1H, s) |
| 144 | 1 | (2,3-dihydrobenzofuran-5-yl) | APN: 330; NMR: 4.62 (2H, t), 7.72 (1H, d), 8.19 (1H, s) |
| 145 | 1 | 3Thie- | APN: 294; NMR: 7.55 (1H, dd), 7.88 (1H, d), 9.22 (1H, s) |

TABLE 11

| Ex | Syn | A | Y | Dat |
|---|---|---|---|---|
| 146 | 1 | Ph- | NMe | AP: 326 (Na); NMR: 4.16 (3H, s), 8.25 (1H, dd), 8.39 (1H, d) |
| 147 | 1 | Ph- | O | APN: 289; NMR: 7.81 (1H, d), 7.97 (1H, s), 8.57 (1H, d) |
| 148 | 1 | 4-Me-Ph- | O | APN: 303; NMR: 2.40 (3H, s), 7.78 (1H, d), 7.91 (1H, s) |
| 149 | 1 | 4-tBu-Ph- | O | APN: 345; NMR: 1.35 (9H, s), 7.80 (1H, d), 7.97 (1H, s) |
| 150 | 1 | 3Thie- | O | APN: 295; NMR: 7.67 (1H, dd), 7.98 (1H, d), 8.03 (1H, s) |
| 151 | 1 | 3Fur- | O | APN: 279; NMR: 7.91 (2H, s), 7.93 (1H, s), 8.50 (1H, d) |
| 152 | 1 | Ph- | S | APN: 305; NMR: 7.78 (1H, d), 8.63 (1H, s), 8.68 (1H,d) |
| 153 | 1 | 4-tBu-Ph- | S | APN: 361; NMR: 1.35 (9H, s), 7.77 (1H, d), 8.62 (1H, s) |

TABLE 12

| No | Str |
|---|---|
| 1 | Ph-(3-cyano-4-phenyl)phenyl-4-hydroxythiazole-5-carboxylic acid |
| 2 | Ph-(3-cyano-4-phenyl)phenyl-1H-pyrazole-5-carboxylic acid |
| 3 | Ph-(3-cyano-4-phenyl)phenyl-3-methyl-1H-pyrazole-4-carboxylic acid |
| 4 | Ph-(3-cyano-4-phenyl)phenyl-3-fluorothiophene-2-carboxylic acid |
| 5 | Ph-(3-cyano-4-phenyl)phenyl-3-fluoropyridine-4-carboxylic acid |

TABLE 12-continued

| No | Str |
|---|---|
| 6 | (structure) |
| 7 | (structure) |
| 8 | (structure) |
| 9 | (structure) |
| 10 | (structure) |
| 11 | (structure) |
| 12 | (structure) |
| 13 | (structure) |
| 14 | (structure) |
| 15 | (structure) |
| 16 | (structure) |
| 17 | (structure) |
| 18 | (structure) |
| 19 | (structure) |
| 20 | (structure) |

TABLE 13

| No | Str |
|---|---|
| 21 | (structure) |
| 22 | (structure) |
| 23 | (structure) |

TABLE 13-continued

| No | Str |
|----|-----|
| 24 | 4'-MeO, 2-CN biphenyl-4-yl linked to N-pyrazole-3-Me-4-CO₂H |
| 25 | 4'-Me, 2-CN biphenyl-4-yl linked to N-pyrazole-3-Me-4-CO₂H |
| 26 | 3'-Me, 2-CN biphenyl-4-yl linked to N-pyrazole-3-Me-4-CO₂H |
| 27 | 3'-CF₃O, 2-CN biphenyl-4-yl linked to 1H-pyrazole-5-CO₂H |
| 28 | 3'-Me, 2-CN biphenyl-4-yl linked to 1H-pyrazole-5-CO₂H |
| 29 | 4'-Me, 2-CN biphenyl-4-yl linked to 1H-pyrazole-5-CO₂H |
| 30 | 4'-MeO, 2-CN biphenyl-4-yl linked to 1H-pyrazole-5-CO₂H |
| 31 | 4'-MeO, 2-CN biphenyl-4-yl linked to thiazole-4-CO₂H |
| 32 | 4'-Me, 2-CN biphenyl-4-yl linked to thiazole-4-CO₂H |
| 33 | 3'-Me, 2-CN biphenyl-4-yl linked to thiazole-4-CO₂H |
| 34 | 3'-CF₃O, 2-CN biphenyl-4-yl linked to thiazole-4-CO₂H |
| 35 | 4'-CF₃O, 2-CN biphenyl-4-yl linked to thiazole-4-CO₂H |
| 36 | 3'-CF₃O, 2-CN biphenyl-4-yl linked to N-Me-pyrazole-5-CO₂H |
| 37 | 3'-Me, 2-CN biphenyl-4-yl linked to N-Me-pyrazole-5-CO₂H |
| 38 | 4'-Me, 2-CN biphenyl-4-yl linked to N-Me-pyrazole-5-CO₂H |
| 39 | 4'-MeO, 2-CN biphenyl-4-yl linked to N-Me-pyrazole-5-CO₂H |
| 40 | 4'-MeO, 2-CN biphenyl-4-yl linked to isothiazole-5-CO₂H |

INDUSTRIAL APPLICABILITY

The compounds of the present invention have a potent xanthine oxidase inhibiting action, and are especially useful as an agent for treating or preventing hyperuricemia, gout, inflammatory bowel disease, diabetic nephropathy, diabetic retinopathy.

The invention claimed is:
1. A triarylcarboxylic acid compound represented by the following formula (I) or a salt thereof:

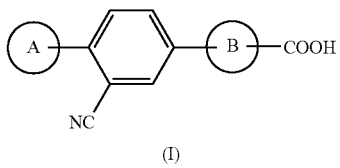

[Formula 11]

(I)

wherein:
A: aryl or heteroaryl,
wherein aryl and heteroaryl may be substituted with the same or different, 1 to 3 substituents selected from the following group G;
group G: halogen, —CN, —NO$_2$, lower alkyl, halogeno-lower alkyl, —O—R$^1$, —O-halogeno-lower alkyl, —O—CO—R$^1$, —O-benzyl, —O-phenyl, —NR$^2$R$^3$, —NH—CO—R$^1$, —CO$_2$—R$^1$, —CO—R$^1$, —CO—NR$^2$R$^3$, —CO-phenyl, —S—R$^1$, —SO$_2$-lower alkyl, —SO$_2$-phenyl, —NH—SO$_2$-naphthalene-NR$^2$R$^3$, phenyl, cycloalkyl, and -lower alkylene-O—R$^1$;
R$^1$: H or lower alkyl;
R$^2$ and R$^3$: same or different, each representing H or lower alkyl,
wherein R$^2$ and R$^3$, taken together with the nitrogen atom to which they bond, may form a monocyclic nitrogen-containing saturated heterocycle; and
B: monocyclic heteroaryl, wherein the monocyclic heteroaryl may be substituted with a group selected from lower alkyl, —OH, and halogen.

2. The triarylcarboxylic acid compound or a salt thereof according to claim 1, wherein A is a ring group selected from phenyl, naphthyl, thienyl, pyridyl, furyl, benzothienyl, benzofuryl and 2,3-dihydrobenzofuran-5-yl and optionally substituted with substituent(s) of the group G.

3. The triarylcarboxylic acid compound or a salt thereof according to claim 1, wherein A is phenyl optionally substituted with substituent(s) of the group G.

4. The triarylcarboxylic acid compound or a salt thereof according to claim 3, wherein the benzene ring and the carboxyl group on the ring group B bond to the ring group B at positions not adjacent to each other.

5. The triarylcarboxylic acid compound or a salt thereof according to claim 4, wherein B is a divalent group of the following formula:

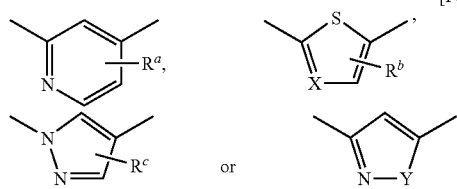

[Formula 12]

where:
X: CH or N,
Y: O, S or NR$^d$,
R$^a$, R$^b$ and R$^c$: H or methyl, and
R$^d$: H or methyl.

6. The triarylcarboxylic acid compound or a salt thereof according to claim 5, wherein B is a ring group selected from pyridine, thiophene, thiazole, isothiazole and pyrazole rings.

7. The triarylcarboxylic acid compound or a salt thereof according to claim 6, wherein the substituents of the group G are halogen, —CN, lower alkyl, halogeno-lower alkyl, —O—R$^1$, —O-halogeno-lower alkyl, —S—R$^1$, —NR$^2$R$^3$, —CO$_2$—R$^1$, and -lower alkylene-O—R$^1$.

8. The triarylcarboxylic acid compound or a pharmaceutically acceptable salt thereof according to claim 1, which is selected from a the group consisting of 2-(2-cyanobiphenyl-4-yl)isonicotinic acid, 2-(2-cyano-4'-methoxybiphenyl-4-yl)isonicotinic acid, 2-(4'-chloro-2-cyanobiphenyl-4-yl)isonicotinic acid, 5-(2-cyanobiphenyl-4-yl)thiophene-2-carboxylic acid, 2-(2-cyano-4'-methylbiphenyl-4-yl)-4-methyl-1,3-thiazole-5-carboxylic acid, 2-(2-cyanobiphenyl-4-yl)-4-methyl-1,3-thiazole-5-carboxylic acid, 2-[2-cyano-4'-(trifluoromethoxy)biphenyl-4-yl]-4-methyl-1,3-thiazole-5-carboxylic acid, 2-(2-cyano-4'-methoxybiphenyl-4-yl)-4-methyl-1,3-thiazole-5-carboxylic acid, 2-(2-cyano-3'-methoxybiphenyl-4-yl)-4-methyl-1,3-thiazole-5-carboxylic acid, 2-(2-cyano-3'-methylbiphenyl-4-yl)-4-methyl-1,3-thiazole-5-carboxylic acid, 1-(2-cyanobiphenyl-4-yl)-1H-pyrazole-4-carboxylic acid, 1-(2-cyano-4'-methylbiphenyl-4-yl)-1H-pyrazole-4-carboxylic acid, 1-(2-cyano-4'-methoxybiphenyl-4-yl)-1H-pyrazole-4-carboxylic acid, 2-(2-cyanobiphenyl-4-yl)-1,3-thiazole-5-carboxylic acid, 3-(2-cyanobiphenyl-4-yl)isothiazole-5-carboxylic acid, 3-(4'-tert-butyl-2-cyanobiphenyl-4-yl)isothiazole-5-carboxylic acid, 3-(2-cyanobiphenyl-4-yl)-1-methyl-1H-pyrazole-5-carboxylic acid, 2-(2-cyano-4'-ethylbiphenyl-4-yl)-4-methyl-1,3-thiazole-5-carboxylic acid, 1-(2-cyano-3'-methylbiphenyl-4-yl)-1H-pyrazole-4-carboxylic acid, and 2-[2-cyano-4'-(dimethylamino)biphenyl-4-yl]-4-methyl-1,3-thiazole-5-carboxylic acid.

9. A pharmaceutical composition comprising a triarylcarboxylic acid compound or a pharmaceutically acceptable salt thereof according to claim 1 and a pharmaceutically acceptable carrier.

10. The pharmaceutical composition as claimed in claim 9, which is a xanthine oxidase inhibitor.

11. The pharmaceutical composition as claimed in claim 9, which is an agent for or treating hyperuricemia, gout, inflammatory bowel disease, diabetic nephropathy, or diabetic retinopathy.

12. A method for treating hyperuricemia, gout, inflammatory bowel disease, diabetic nephropathy, or diabetic retinopathy, which comprises administering a therapeutically effective amount of a triarylcarboxylic acid compound or a pharmaceutically acceptable salt thereof according to claim 1, to a patient.

13. 2-(2-cyanobiphenyl-4-yl)isonicotinic acid.
14. 2-(2-cyanobiphenyl-4-yl)-4-methyl-1,3-thiazole-5-carboxylic acid.
15. 1-(2-cyanobiphenyl-4-yl)-1H-pyrazole-4-carboxylic acid.
16. 1-(2-cyano-4'-methylbiphenyl-4-yl)-1H-pyrazole-4-carboxylic acid.
17. 1-(2-cyano-4'-methoxybiphenyl-4-yl)-1H-pyrazole-4-carboxylic acid.
18. 2-(2-cyanobiphenyl-4-yl)-1,3-thiazole-5-carboxylic acid.
19. A pharmaceutical composition comprising a triarylcarboxylic acid compound or a pharmaceutically acceptable salt thereof according to claim 8 and a pharmaceutically acceptable carrier.

* * * * *